United States Patent
Schmidt et al.

(10) Patent No.: US 11,913,941 B2
(45) Date of Patent: Feb. 27, 2024

(54) SYSTEMS AND METHODS OF DELIVERING TARGET MOLECULES TO A NANOPORE

(71) Applicants: The Regents of the University of California, Oakland, CA (US); Brigham Young University, Provo, UT (US)

(72) Inventors: Holger Schmidt, Capitola, CA (US); Aaron Roe Hawkins, Provo, UT (US); David W. Deamer, Santa Cruz, CA (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 658 days.

(21) Appl. No.: 16/652,381

(22) PCT Filed: Oct. 2, 2018

(86) PCT No.: PCT/US2018/053946
§ 371 (c)(1),
(2) Date: Mar. 30, 2020

(87) PCT Pub. No.: WO2019/070692
PCT Pub. Date: Apr. 11, 2019

(65) Prior Publication Data
US 2020/0284783 A1 Sep. 10, 2020

Related U.S. Application Data

(60) Provisional application No. 62/566,983, filed on Oct. 2, 2017.

(51) Int. Cl.
*G01N 33/53* (2006.01)
*B01L 3/00* (2006.01)
(Continued)

(52) U.S. Cl.
CPC ...... *G01N 33/5302* (2013.01); *B01L 3/50273* (2013.01); *C12Q 1/6825* (2013.01);
(Continued)

(58) Field of Classification Search
CPC ......... G01N 33/5302; G01N 33/48721; G01N 33/54333; G01N 2035/00247;
(Continued)

(56) References Cited

U.S. PATENT DOCUMENTS 9,515,159 B2 12/2016 Bischopink et al.
2006/0231419 A1* 10/2006 Barth .................. B82Y 5/00
205/775

(Continued)

FOREIGN PATENT DOCUMENTS

WO      2010117470 A2    10/2010
WO    WO 2017/164514 A1    9/2017

OTHER PUBLICATIONS

International Patent Application No. PCT/US2018/053946; Int'l Search Report; dated Jan. 17, 2019; 4 pages.
(Continued)

*Primary Examiner* — Christine T Mui
(74) *Attorney, Agent, or Firm* — Carter, DeLuca & Farrell LLP

(57) ABSTRACT

A disclosed system uses modulations of ionic current across a nanopore in a membrane to detect target molecules passing through the nanopore. This principle has been applied mainly to nucleic acid sequencing, but can also be used to detect other molecular targets such as proteins and small molecules. In addition, the system delivers target molecules to a nanopore to provide label-free single molecule analysis using a chip-based system. Target molecules are concentrated on microscale carrier beads, and the beads are delivered and optically trapped in an area within the capture
(Continued)

radius of the nanopore. The target molecules are released from the beads and detected using nanopore current modulation. In addition, the disclosed system combines sample preparation (e.g. purification, extraction, and pre-concentration) with nanopore-based readout on a microfluidic chip. Finally, target molecules can be specifically bound to carrier beads and particles are positioned within the capture volume of a nanopore using a chip-based microfluidic platform proven to handle specific detection of molecular targets from milliliters of raw sample.

18 Claims, 12 Drawing Sheets

(51) Int. Cl.
| | |
|---|---|
| C12Q 1/70 | (2006.01) |
| G01N 33/487 | (2006.01) |
| C12Q 1/6825 | (2018.01) |
| G01N 35/00 | (2006.01) |
| G01N 33/543 | (2006.01) |

(52) U.S. Cl.
CPC ......... *C12Q 1/70* (2013.01); *G01N 33/48721* (2013.01); *G01N 33/54333* (2013.01); *G01N 35/00* (2013.01); *B01L 2200/0668* (2013.01); *G01N 2035/00247* (2013.01)

(58) Field of Classification Search
CPC ......... B01L 3/50273; B01L 2200/0668; C12Q 1/6825; C12Q 1/70
USPC ....................................................... 436/518
See application file for complete search history.

(56) References Cited

U.S. PATENT DOCUMENTS

| | | | | |
|---|---|---|---|---|
| 2008/0041733 | A1* | 2/2008 | Hibbs | C12Q 1/6869 |
| | | | | 204/403.01 |
| 2008/0254995 | A1* | 10/2008 | Kim | B82Y 30/00 |
| | | | | 506/7 |
| 2017/0234850 | A1 | 8/2017 | Morin | |

OTHER PUBLICATIONS

International Patent Application No. PCT/US2018/053946; Int'l Preliminary Report on Patentability; dated Apr. 16, 2020; 8 pages.
Hamburg et al.; "The Path to Personalized Medicine"; The New England Journal of Medicine; vol. 363; 2010; p. 301-304 (abstract only).
Ziegler et al.; "Personalized medicine using DNA biomarkers: a review"; Human Genetics; vol. 131; 2012; p. 1627-1638.
Euan a. Ashley; "Towards precision medicine"; Nature Reviews Genetics; vol. 17; 2016; p. 507-522 (abstract only).
Manuel L. Gonzalez-Garay; "The road from next-generation sequencing to personalized medicine"; Personalized Medicine; vol. 11; 2014; p. 523-544.
Frei et al.; "Highly multiplexed simultaneous detection of RNAs and proteins in single cells"; Nature Methods; vol. 269; Mar. 2016; p. 269-275.
https://www.euroimmun.com/products/indications/infektions-serologie/zika-viruses.html; Antibodies against zika viruses; Euroimmun a PerkinElmer Company; accessed May 15, 2020; 12 pages.
Chiu et al.; "Experimental Zika Virus Inoculation in a New World Monkey Model Reproduces Key Features of the Human Infection"; Scientific Reports; vol. 7; 2017; 11 pages.
Huzly et al.; "High specificity of a novel Zika virus ELISA in European patients after exposure to different flaviviruses"; Eurosurveillance; vol. 21; 2016; 4 pages.

Michael T. Osterholm; "Ebola and Zika: Cautionary tales"; Science; vol. 353; Sep. 2016; p. 1073.
Lanciotti et al.; "Genetic and Serologic Properties of Zika Virus Associated with an Epidemic, Yap State, Micronesia, 2007"; Emerging Infectious Diseases; vol. 14; Aug. 2008; p. 1232-1239.
Waggoner et al.; "Zika Virus: Diagnostics for an Emerging Pandemic Threat"; Journal of Clinical Microbiology; vol. 54; Apr. 2016; p. 860-867.
Cornish et al.; "A Survey of Single-Molecule Techniques in Chemical Biology"; ACS Chem. Biol.; vol. 2; 2007; p. 53-61 (abstract only).
Schuler et al.; "Protein folding studied by single-molecule FRET"; Current Opinion in Structural Biology; vol. 18; Feb. 2008; p. 16-26.
Rhoades et al.; "Watching proteins fold one molecule at a time"; PNAS; vol. 100; 2003; p. 3197-3202.
Seisenberger et al.; "Real-Time Single-Molecule Imaging of the Infection Pathway of an Adeno-Associated Virus"; Science; vol. 294; 2001; p. 1929-1932 (abstract only).
Chang et al.; "Single-Molecule Analysis of Human Immunodeficiency Virus Type 1 gp120-Receptor Interactions in Living Cells"; Journal of Virology; vol. 79; Dec. 2005; p. 14748-14755.
Bustamante et al.; "Ten years of tension: single-molecule DNA mechanics"; Nature; vol. 421; Jan. 2003; p. 423-427.
Levene et al.; "Zero-Mode Waveguides for Single-Molecule Analysis at High Concentrations"; Science; vol. 299; Jan. 2003; p. 682-686.
Eid et al.; "Real-Time DNA Sequencing from Single Polymerase Molecules"; Science; vol. 323; Jan. 2009; p. 133-138.
Kasianowicz et al.; "Characterization of individual polynucleotide molecules using a membrane channel"; Proc. Natl. Acad. Sci. USA; vol. 93; Nov. 1996; p. 13770-13773.
Clarke et al.; "Continuous base identification for single-molecule nanopore DNA sequencing"; Nature Nanotechnology; vol. 4; Apr. 2009; p. 265-270.
Joe Howard; "Molecular motors: structural adaptations to cellular functions" Nature; vol. 389; Oct. 1997; p. 561-567.
Svoboda et. al.; "Direct observation of kinesin stepping by optical trapping interferometry"; Nature; vol. 365; 1993; p. 721-727 (abstract only).
Finer et al.; "Single myosin molecule mechanics: piconewton forces and nanometre steps"; Nature; vol. 368; Mar. 1994; p. 113-119.
Meyhofer et al.; "The force generated by a single kinesin molecule against an elastic load"; Proc. Natl. Acad. Sci. USA; vol. 92; Jan. 1995; p. 574-578.
Funatsu et al.; "Imaging of single fluorescent molecules and individual ATP turnovers by single myosin molecules in aqueous solution"; Nature; vol. 374; 1995; p. 555-559 (abstract only).
Wieser et al.; "Tracking single molecules in the live cell plasma membrane—Do's and Don't's"; Methods; vol. 46; Oct. 2008; p. 131-140.
Kusumi et al.; "Single-molecule tracking of membrane molecules: plasma membrane compartmentalization and dynamic assembly of raft-philic signaling molecules"; Seminars in Immunology; vol. 17; Feb. 2005; p. 3-21.
http://www.pacb.com/; Pacbio; © 2015-2020; accessed May 15, 2020; 5 pages.
http://www.bio-rad.com/en-us/applications-technologies/introduction-digital-pcr; Introduction to Digital PCR; BIO-RAD; © 2020; accessed May 15, 2020; 5 pages.
Branton et al.; "Characterization of Nucleic Acids by Nanopore Analysis"; Acc. Chem. Res.; vol. 35; 2002; p. 817-825.
Branton et al.; "The potential and challenges of nanopore sequencing"; Nat Biotechnol.; vol. 26; Oct. 2008; p. 1146-1153.
Howorka et al.; "Nanopore analytics: sensing of single molecules"; Chemical Society Review; Issue 8; 2009; p. 2360-2384 (abstract only).
Feng et al. "Nanopore-based Fourth-generation DNA Sequencing Technology"; Genomics, Proteomics & Bioinformatics; vol. 13; Feb. 2015; p. 4-16.
Deamer et al.; "Three decades of nanopore sequencing"; Nature Biotechnology; vol. 34; May 2016; p. 518-524.

(56) References Cited

OTHER PUBLICATIONS

Han et al.; "Label-Free Detection of Single Protein Molecules and Protein-Protein Interactions Using Synthetic Nanopores"; Anal. Chem.; vol. 80; 2008; p. 4651-4658.

Muthukumar et al.; "Theory of capture rate in polymer translocation"; The Journal of Chemical Physics; vol. 132; 2010; 195101 p. 10 pages.

Wanunu et al.; "Electrostatic focusing of unlabelled DNA into nanoscale pores using a salt gradient"; Nature Nanotechnology; vol. 5; Feb. 2010; p. 160-165.

Maglia et al.; "Enhanced translocation of single DNA molecules through α-hemolysin nanopores by manipulation of internal charge"; PNAS; vol. 105; Dec. 2008; p. 19720-19725.

Laszlo et al.; "Decoding long nanopore sequencing reads of natural DNA"; Nature Biotechnology; vol. 32; Aug. 2014; p. 829-833.

Lu et al.; "Pressure-Controlled Motion of Single Polymers through Solid-State Nanopores"; Nano Letters; vol. 13; Jul. 2013; p. 3048-3052.

Freeman et al.; "Nanopore sensing at ultra-low concentrations using single-molecule dielectrophoretic trapping"; Nature Communications; vol. 7; 2016; 9 pages.

Carron Jr. et al.; "An animal model that reflects human disease: the common marmoset (*Callithrix jacchus*)"; Current Opinion in Virology; vol. 2; Jun. 2012; p. 357-362.

Chang et al.; "DNA-Mediated Fluctuations in Ionic Current through Silicon Oxide Nanopore Channels"; Nano Letters; vol. 4; 2004; p. 1551-1556.

Li et al.; "Ion-beam sculpting at nanometre length scales"; Nature; vol. 412; 2001; p. 166-169.

Storm et al.; "Fabrication of solid-state nanopores with single-nanometre precision"; Nature Materials; vol. 2; Aug. 2003; p. 537-540.

Cees Dekker; "Solid-state nanopores"; Nature Nanotechnology; vol. 2; 2007; p. 209-215.

Bacri et al.; "Dynamics of Colloids in Single Solid-State Nanopores"; J. Phys. Chem. B; vol. 115; 2011; p. 2890-2898 (abstract only).

Barzon et al.; "Isolation of infectious Zika virus from saliva and prolonged viral RNA shedding in a traveller returning from the Dominican Republic to Italy, Jan. 2016"; Eurosurveillance; vol. 21; 2016; 30159; 5 pages.

Gourinat et al.; "Detection of Zika Virus in Urine"; Emgerging Infectious Diseases; vol. 21; Jan. 2015; p. 84-86.

Watzinger et al.; "Detection and monitoring of virus infections by real-time PCR"; Molecular Aspects of Medicine; vol. 27; 2006; p. 254-298.

Towner et al.; "Rapid Diagnosis of Ebola Hemorrhagic Fever by Reverse Transcription-PCR in an Outbreak Setting and Assessment of Patient Viral Load as a Predictor of Outcome"; Journal of Virology; vol. 78; Apr. 2004; p. 4330-4341.

Kuypers et al.; "Comparison of Real-Time PCR Assays with Fluorescent-Antibody Assays for Diagnosis of Respiratory Virus Infections in Children"; Journal of Clinical Microbiology; vol. 44; Jul. 2006; p. 2382-2388.

Duan et al.; "Fabrication of nanofluidic devices"; Biomicrofluidics; vol. 7; 2013; 41 pages.

Schmidt et al.; "Optofluidic waveguides: I. Concepts and implementations"; Microfluidics and Nanofluidics; vol. 4; Jan. 2008; p. 3-16.

Hawkins et al.; "Optofluidic waveguides: II. Fabrication and structures"; Microfluidics and Nanofluidics; vol. 4; Jul. 2007; p. 17-32.

Schmidt et al.; "Hollow-core waveguides and 2-D waveguide arrays for integrated optics of gases and liquids"; IEEE Journal of Selected Topics in Quantum Electronics; vol. 11; 2005; p. 519-527 (abstract only).

Yin et al.; "Microphotonic control of single molecule fluorescence correlation spectroscopy using planar optofluidics"; Optics Express; vol. 15; Jun. 2007; p. 7290-7295.

Yin et al.; "Single-molecule detection sensitivity using planar integrated optics on a chip"; Optics Express; vol. 31; 2006; p. 2136-2138 (abstract only).

Parks et al.; "Hybrid optofluidic integration"; Lab on a Chip; vol. 13; Oct. 2013; p. 4118-4123.

Parks et al.; "Integration of programmable microfluidics and on-chip fluorescence detection for biosensing applications"; Biomicrofluidics; vol. 8; 2014; 8 pages.

Cai et al.; "Optofluidic analysis system for amplification-free, direct detection of Ebola infection"; Scientific Reports; vol. 5; 2015; 8 pages.

Ozcelik et al.; "Optofluidic wavelength division multiplexing for single-virus detection"; PNAS; vol. 112; Oct. 2015; p. 12933-12937.

Lui et al.; "Correlated Electrical and Optical Analysis of Single Nanoparticles and Biomolecules on a Nanopore-Gated Optofluidic Chip"; Nano Letters; vol. 14; 2014; p. 4816-4820.

Liu et al.; "Electro-optical detection of single λ-DNA"; Chemical Communications; vol. 51; Feb. 2015; p. 2084-2087.

Liu et al.; "Optofluidic devices with integrated solid-state nanopores"; Microchimica Acta; vol. 183; Apr. 2016; p. 1275-1287.

Ozcelik et al.; "Scalable Spatial-Spectral Multiplexing of Single-Virus Detection Using Multimode Interference Waveguides"; Scientific Reports; vol. 7; 2017; 8 pages.

Barber et al.; "Fabrication of hollow waveguides with sacrificial aluminum cores"; IEEE Photonics Technology Letters; vol. 17; Feb. 2005; p. 363-365.

Barber et al.; "Integrated hollow waveguides with arch-shaped cores"; IEEE Photonics Technology Letters; vol. 18; 2006; p. 28-30 (abstract only).

Hubbard et al.; "Mechanical models and design rules for on-chip micro-channels with sacrificial cores"; Journal of Micromechanics and Microengineering; vol. 15; 2005; p. 720 (abstract only).

Lunt et al.; "Improving solid to hollow core transmission for integrated ARROW waveguides"; Optics Express; vol. 16; Dec. 2008; p. 20981-20986.

Lunt et al.; "Improving Hollow Waveguides on Self-Aligned Pedestals for Improved Geometry and Transmission" IEEE Phot. Tech. Letters; vol. 22; 2010; p. 1147-1149.

Zhao et al.; "Hollow waveguides with low intrinsic photoluminescence fabricated with Ta2O5 and SiO2 films"; Applied Physics Letters; vol. 98; 2011; 3 pages.

Zhao et al.; "Optimization of Interface Transmission Between Integrated Solid Core and Optofluidic Waveguides"; IEEE Photonics Technology Letters; vol. 24; Jan. 2012; p. 46-48.

Du et al.; "Multiplexed efficient on-chip sample preparation and sensitive amplification-free detection of Ebola virus"; Biosensors and Bioelectronics; vol. 91; May 2017; p. 489-496.

Du et al.; "Microfluidic System for Detection of Viral RNA in Blood Using a Barcode Fluorescence Reporter and a Photocleavable Capture Probe"; Anal. Chem.; vol. 89; Nov. 2017; p. 12433-12440.

Cai et al.; "On-chip wavelength multiplexed detection of cancer DNA biomarkers in blood"; Biomicrofluidics; vol. 10; 2016; 064116; 9 pages.

Holmes et al.; "Micropore and nanopore fabrication in hollow antiresonant reflecting optical waveguides"; Journal of Micro/Nanolithography MEMS and MOEMS; vol. 9; 2010; 14 pages.

Rudenko et al.; "Controlled gating and electrical detection of single 50S ribosomal subunits through a solid-state nanopore in a microfluidic chip"; Biosensors and Bioelectronics; vol. 29; Nov. 2011; p. 34-39.

Liu et al.; "Effect of Fabrication-Dependent Shape and Composition of Solid-State Nanopores on Single Nanoparticle Detection"; ACS Nano; vol. 7; Jun. 2013; p. 5621-5627.

Brasil et al.; "Zika Virus Infection in Pregnant Women in Rio de Janeiro"; The New England Journal of Medicine; vol. 375; Dec. 2016; p. 2321-2334.

Corman et al.; "Assay optimization for molecular detection of Zika virus"; Bull World Health Organ; vol. 94; 2016; p. 880-892.

Barzon et al.; "Infection dynamics in a traveller with persistent shedding of Zika virus RNA in semen for six months after returning from Haiti to Italy, Jan. 2016"; Eurosurveillance; vol. 21; Aug. 2016; 4 pages.

Parks et al; "Dual detection of Zika virus nucleic acid and protein using a multi-mode interference waveguide platform"; IEEE Photonics Conf.; 2017; (abstract only).

(56) References Cited

OTHER PUBLICATIONS

Measor et al.; "Hollow-core waveguide characterization by optically induced particle transport"; Optics Letters; vol. 33; Apr. 2008; p. 672-674.
Measor et al.; "Multi-mode mitigation in an optofluidic chip for particle manipulation and sensing"; Optics Express; vol. 17; Dec. 2009; p. 24342-24348.
Kuhn et al.; "Loss-based optical trap for on-chip particle analysis"; Lab on a Chip; vol. 9; Aug. 2009; p. 2212-2216.
Kuhn et al.; "Optofluidic particle concentration by a long-range dual-beam trap"; Optics Letters; vol. 34; Aug. 2009; p. 2306-2308.
Kuhn et al.; "Ultralow power trapping and fluorescence detection of single particles on an optofluidic chip"; Lab on a Chip; vol. 10; Jan. 2010; p. 189-194.
Song et al.; "Zika virus NS1 structure reveals diversity of electrostatic surfaces among flaviviruses"; Nature Structural & molecular biology; vol. 23; 2016; p. 456-458.
Kumar et al.; "Thin-film microfabricated nanofluidic arrays for size-selective protein fractionation"; Lab on a Chip; vol. 13; Dec. 2013; p. 4591-4598.
Nam et al.; "Nanoparticle-Based Bio-Bar Codes for the Ultrasensitive Detection of Proteins"; Science; vol. 301; Sep. 2003; p. 1884-1886.
Boonjob; "An Overview about Recent Advances of Micro-Solid Phase Extraction in Flow Based Techniques"; Austin J. Anal. Pharm. Chem; vol. 1; 2014; 6 pages.
Hwang et al.; "Solid Phase DNA Extraction with a Flexible Bead-Packed Microfluidic Device to Detect Methicillin-Resistant *Staphylococcus aureus* in Nasal Swabs"; Anal. Chem.; vol. 84; 2012; p. 7912-7918 (abstract only).
Bylda et al.; "Recent advances in sample preparation techniques to overcome difficulties encountered during quantitative analysis of small molecules from biofluids using LC-MS/MS"; Analyst; vol. 139; 2014; p. 2265-2276.
Safarik et al.; "Magnetic techniques for the isolation and purification of proteins and peptides"; BioMagnetic Research and Technology; vol. 2; 2004; 17 pages.
Odabasi et al.; "Polyhydroxyethylmethacrylate-based magnetic DNA-affinity beads for anti-DNA antibody removal from systemic lupus erythematosus patient plasma"; Journal of Chromatography B: Biomedical Sciences and Applications; vol. 760; Aug. 2001; p. 137-148 (abstract only).
Quitadamo et al.; "Magnetic bead purification as a rapid and efficient method for enhanced antibody specificity for plant sample immunoblotting and immunolocalization"; Plant Science; vol. 153; Apr. 2000; p. 7-14 (abstract only).
Ozkara et al.; "A Novel Magnetic Adsorbent for Immunoglobulin-G Purification in a Magnetically Stabilized Fluidized Bed"; Biotechnology Progress; vol. 20; 2004; p. 1169-1175 (abstract only).
https://zika.labkey.com/project/oconnor/ZIKV-001/begin.view; LabKey Open Research Portal; accessed Sep. 23, 2020; 11 pages.
http://www.biofronttech.com/product/research-reagents-zika-virus-reagents-zika-virus-ns1-elisa/zika-virus-ns1-elisa/1607015/; Zika Virus NS1 Elisa; BioFront Technologies; © 2020; accessed May 15, 2020; 5 pages.
Schudel et al.; "Microfluidic chip for combinatorial mixing and screening of assays"; Lab Chip; vol. 9; 2009; p. 1676-1680.
Kim et al.; "Lifting Gate Polydimethylsiloxane Microvalves and Pumps for Microfluidic Control"; Analytical Chemistry; vol. 84; Feb. 2012; p. 2067-2071.
Kim et al.; "Pneumatically actuated microvalve circuits for programmable automation of chemical and biochemical analysis"; Lab on a Chip; vol. 16; 2016; p. 812-819 (abstract only).
Larsen et al.; "Protein and cell patterning in closed polymer channels by photoimmobilizing proteins on photografted poly(ethylene glycol) diacrylate"; Biomicrofluidics; vol. 8; 2014; 064127; 11 pages.
Ruiz-Taylor et al.; "X-ray Photoelectron Spectroscopy and Radiometry Studies of Biotin-Derivatized Poly(l-lysine)-grafted-Poly(ethylene glycol) Monolayers on Metal Oxides"; Langmuir; vol. 17; 2001; p. 7313-7322 (abstract only).
Ruiz-Taylor et al.; "Monolayers of derivatized poly(l-lysine)-grafted poly(ethylene glycol) on metal oxides as a class of biomolecular interfaces"; PNAS; vol. 98; Jan. 2001; p. 852-857.
Yang et al.; "Surface modification on polydimethylsiloxane-based microchannels with fragmented poly(l-lactic acid) nanosheets"; Biomicrofluidics; vol. 9; 2015; 064108; 9 pages.
Shin et al.; "PDMS-based micro PCR chip with Parylene coating"; Journal of Micromechanics and Microengineering; vol. 13; 2003; p. 768-774.
Extended European Report dated May 7, 2021 issued in corresponding EP Appln. No. 18865160.8.
Sischka, Andy et al. "Single Beam Optical Tweezers Setup with Backscattered Light Detection for Three-Dimensional Measurements on DNA and Nanopores", Review of Scientific Instruments, AIP, Melville, NY, vol. 79, No. 6, Jun. 18, 2008, pp. 63702-63702.
Kovarik, Michelle L. et al., "Nanopore Devices for AC Electrokinetic Trapping", 11th International Conference on Minaturized Systems for Chemistry and Life Aciences, Microtas 2007, Paris, France, Oct. 7, 2007.
Takayuki, Hoshino, et al., "Electron Beam Switched Trapping and Release of Nanoparticles on Nanopore Array", 2015, 28th IEEE International Conference on Micro Electro Mechanical Systems (MEMS), IEEE, Jan. 18, 2015, pp. 512-515.
https://www.euroimmun.com/fileadmin/zika/12df/Zika-Serological diffential diagnosis ELISA-EUROIMMUN.pdf, retrieved Feb. 28, 2023.
https://www.singulex.com/technology-science (web address not valid anymore) retrieved Feb. 28, 2023.
https://www.thenanoporesite.com/groups--companies.html (web address not valid anymore) retrieved Feb. 28, 2023.

* cited by examiner

SYSTEMS AND METHODS OF DELIVERING TARGET MOLECULES TO A NANOPORE

CROSS-REFERENCE TO RELATED APPLICATIONS

This application is the U.S. National Stage of International Application No. PCT/US2018/053946, filed Oct. 2, 2018, titled "SYSTEMS AND METHODS OF DELIVERING TARGET MOLECULES TO A NANOPORE," which claims priority to U.S. provisional patent application No. 62/566,983, titled "SYSTEMS AND METHODS OF DELIVERING TARGET MOLECULES TO A NANOPORE," filed Oct. 2, 2017. All of which are hereby incorporated by reference in their entirety.

BACKGROUND

There is a pressing demand for tools that can simultaneously analyze multiple target molecules (including biomarkers), such as nucleic acids, proteins, and metabolites. In particular, such tools are needed to analyze a variety of genomic and proteomic biomarkers with high specificity and sensitivity at ultra-low concentrations [1-5]. These tools are particularly needed for early disease detection and personalized medicine.

Direct detection of multiple target molecules within a single sample has significant advantages over molecule specific assays, such as DNA amplification and/or protein sandwich assays.

Technologies that detect multiple types of molecules by single-molecule detection and analysis have matured in recent years [13-29], and now forms the core of many next-generation molecular analysis technologies. While most approaches, both on the research and commercial side, have used fluorescent labels, [13-20,27-29,30-32], non-optical techniques have recently gained prominence. One such example involves the electrical detection of single analytes using nanopores in which modulations of ionic current across a nanoscale opening are used to detect particles passing through the pore [33-37]. Such devices can analyze a diverse range of target molecules, some without the need for a fluorescent or other label. While current applications focus on nucleic acid sequencing, the methodologies are also being used for other types of target molecules such as proteins and small molecules [38,39].

SUMMARY

Disclosed herein are systems and methods that use modulations of ionic current across a nanoscale pore (nanopore) in a membrane to detect (including identifying, and/or counting) target molecules passing through the nanopore. This principle has been applied mainly to nucleic acid sequencing, but can also be used to detect other molecular targets such as proteins and small molecules. A challenge faced by nanopore devices is the inefficient delivery of a sufficient number of target molecules to an area sufficiently close to the pore that electrophoretic capture and detection of the target molecules can be achieved. This inefficient delivery limits the throughput (the time of analysis and/or the number of target molecules detected per unit time) and the limit of detection of any assay for a target molecule. Biomarkers that occur in samples at femto- to atto-molar concentrations are unlikely to be detectable without a more efficient delivery of target molecules to the nanopore. [40-45].

Disclosed herein are systems and methods that deliver target molecules to a nanopore to provide label-free single molecule analysis using a chip-based system. The systems and methods involve the concentration of target molecules on microscale carrier beads. The beads are then delivered and optically trapped in an area that is within the capture radius of the nanopore. The target molecules are released from the beads and detected using nanopore current modulation. This approach can locally increase the analyte concentration by up to $10^6$ times, resulting in enhanced throughput and far lower limits of detection than can be achieved using current methods.

Disclosed herein is a system that combines sample preparation (e.g. purification, extraction, and pre-concentration) with nanopore-based readout on a microfluidic chip. In some aspects, a valve-based microfluidic chip using solid-phase extraction loads target analytes onto carrier beads with high specificity. This results in the concentration of targets from mL-scale starting volumes onto beads in order to access clinically relevant concentration ranges in the femto- and attomolar range.

Disclosed herein is a system that involves specifically binding target molecules to carrier beads and positioning the particles within the capture volume of a nanopore using a chip-based microfluidic platform that has been proven to handle specific detection of molecular targets from milliliters of raw sample. In some examples, the microfluidic platform comprises an optofluidic platform as described in U.S. Pat. No. 9,267,891. The target molecules are then released from the beads and detected using the nanopore. The disclosed devices, systems, and methods result in an improvement by up to six orders of magnitude in nanopore capture rate of compared to that of a bulk solution.

DETAILED DESCRIPTION

Figure 1:
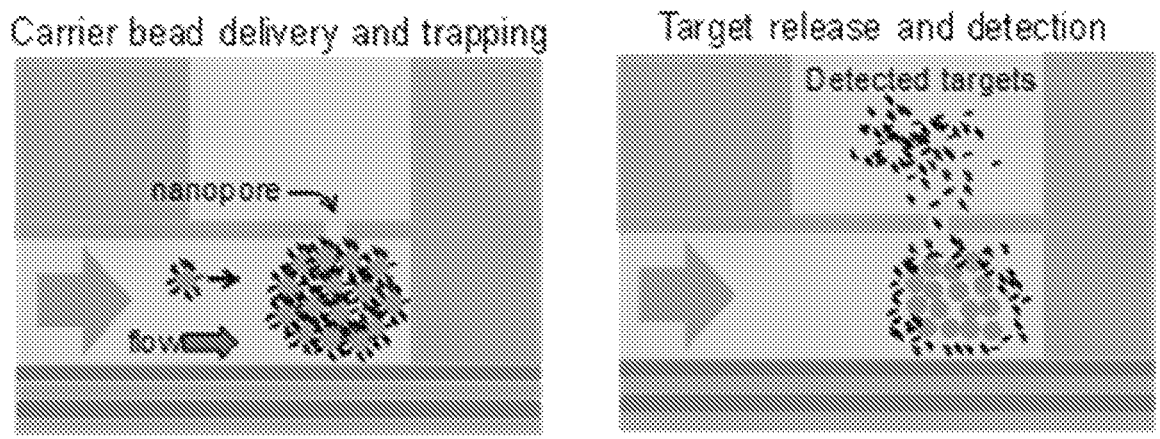
FIG. 1 is a set of two drawings illustrating an embodiment of the disclosed device. The left panel illustrates microbeads carrying target molecules that are concentrated near a nanopore by optical trapping on an optofluidic chip. The right panel illustrates target molecules that are released from carrier beads in close proximity to the nanopore capture volume. The target molecules released from carrier beads are detected a faster rate as they pass through the pore.

Detection of a target molecule by a device comprising a nanopore (a nanopore device) means that the passage of the molecule through the nanopore results in the nanopore device generating a signal. The signal identifies the target molecule passing through the nanopore in that the signal that results from a first target molecule passing through the nanopore can be distinguished from the signal that results from a second target molecule passing through the nanopore. Detection of the target molecule can also involve counting the number of the first and/or second target molecule that pass through the nanopore. One type of target molecule is a biomarker. A biomarker can be any molecular, biological or physical attribute that characterizes a physiological or cellular state and that can be objectively measured to detect or define disease progression or predict or quantify therapeutic responses. A biomarker can be any molecular structure produced by a cell or organism. A biomarker can be expressed inside any cell or tissue, accessible on the surface of a tissue or cell, structurally inherent to a cell or tissue such as a structural component, secreted by a cell or tissue, produced by the breakdown of a cell or tissue through processes such as necrosis, apoptosis or the like, or any combination of these. A biomarker may be any protein, carbohydrate, fat, nucleic acid (including DNA or RNA), catalytic site, or any combination of these such as an enzyme, glycoprotein, cell membrane, virus, cell, organ, organelle, or any uni- or multimolecular structure or any other such structure now known or yet to be disclosed whether alone or in combination. A biomarker can be represented by the sequence of a nucleic acid, a sequence of a protein, or any other chemical structure.

As disclosed herein, a target molecule can be any molecule, nanoparticle, or other structure that can be detected using a nanopore device. Target molecules include nucleic acids such as DNA or RNA, proteins, peptides, small molecules (including naturally occurring and artificial small molecules), or any other molecule that can pass through a nanopore.

An antibody is a polypeptide including at least a light chain or heavy chain immunoglobulin variable region which specifically recognizes and binds an epitope of an antigen or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. The term antibody includes intact immunoglobulins, as well the variants and portions thereof, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies, heteroconjugate antibodies (such as, bispecific antibodies).

A nanopore can be any pore less than about 1 micron in diameter, including at least 1 nm, at least 5 nm, at least 10 nm, at least 20 nm, at least 50 nm, at least 100 nm, at least 250 nm, at least 500 nm, at least 750 nm, or at least 900 nm.

Nanopores can be 1 nm-1 micron in diameter, 1 nm-100 nm, 2 nm-50 nm, 5 nm-20 nm, 10 nm-20 nm, 10 nm-50 nm, 20 nm-75 nm, 40 nm-60 nm, or any intervening range of the aforementioned ranges. A nanopore also includes a pore that is less than 1 inn in diameter on one side of a membrane and greater than 1 μm in diameter on the other side of the membrane.

Binding or stable binding: An association between two substances or molecules, such as the association of a target molecule with a capture molecule conjugated, for example to a bead. Binding can be detected by any procedure known to one skilled in the art, such as by physical or functional properties.

Chip-Based Optofluidic Platforms

Figure 3A:
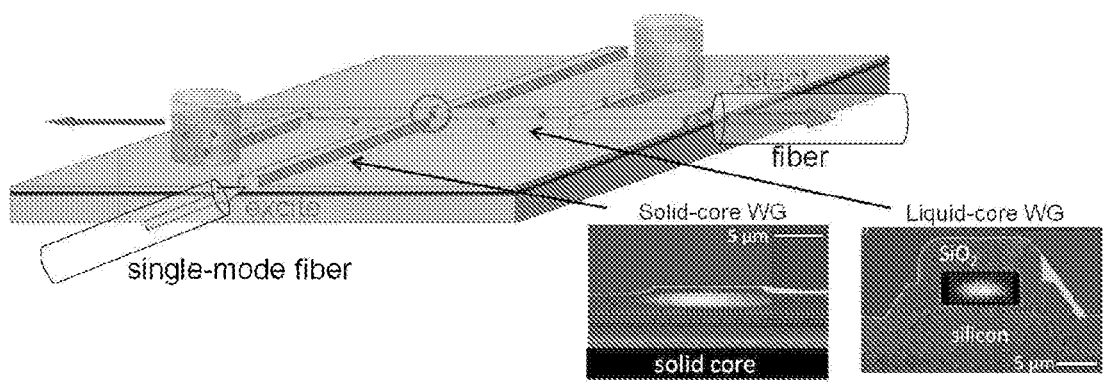
FIG. 3A is a drawing of an optofluidic chip layout (top left) with two images of waveguide cross sections with optical modes (bottom right). Arrows indicate areas on the chip where the images were obtained.

The disclosed systems and methods involve a chip-based optofluidic platform that has been shown to enable both electrical and optical single molecule detection and can be integrated with up-stream sample processing [58-70]. FIG. 3A shows a sample implementation that enables highly efficient interaction of light with molecular targets on a silicon chip.

FIG. 3A shows images of liquid-core waveguides with core dimensions of 5 μm×12 μm (see SEM image with super-imposed image of the guided optical mode) that are interfaced with solid-core ARROW waveguides (FIG. 3A) at different points of the liquid core [58-60]. The channels and waveguides are created using standard microfabrication techniques involving deposition of dielectric layers in combination with sacrificial layer etching. This approach has been proven using different materials (e.g. $SiO_2$, SiN, $Ta_2O_5$) and core shapes [71-77]. For fluorescence detection, excitation light (green arrow) enters the liquid core through an orthogonally intersecting solid-core ARROW where individual targets are excited in femtoliter excitation volumes. Their fluorescence (red arrow) is collected perpendicularly in the chip plane and efficiently guided along the liquid-core channels [62]. This detection chip can be combined with a PDMS-based microfluidic chip (FIG. 2B). The PDMS chip can perform different sample preparation steps [63-65] and can be connected to the optical chip directly or via tubing as shown. This system can be used to detect specific molecules, including amplification-free, highly specific detection of Ebola virus RNAs from clinical samples [65,78,79], individual virus particles [66], and multiplexed cancer biomarkers [69].

Nanopore Detection Principle and Limitations for High Throughput/Low LoD

Figure 2A:
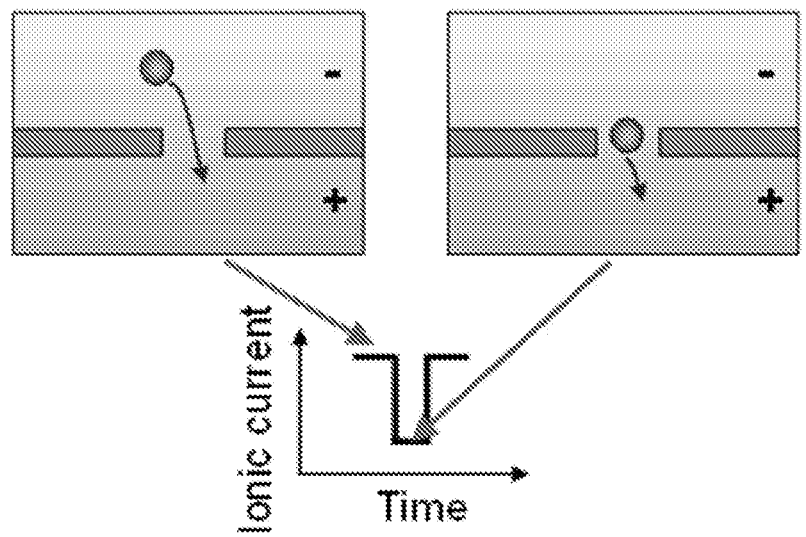
FIG. 2A is a set of two top panels and a bottom panel that illustrate the principle behind nanopore detection. In particular, a particle moving through a nanopore under applied bias (top left and top right panels) causes a change in ionic current across membrane (bottom panel).
Figure 2B:
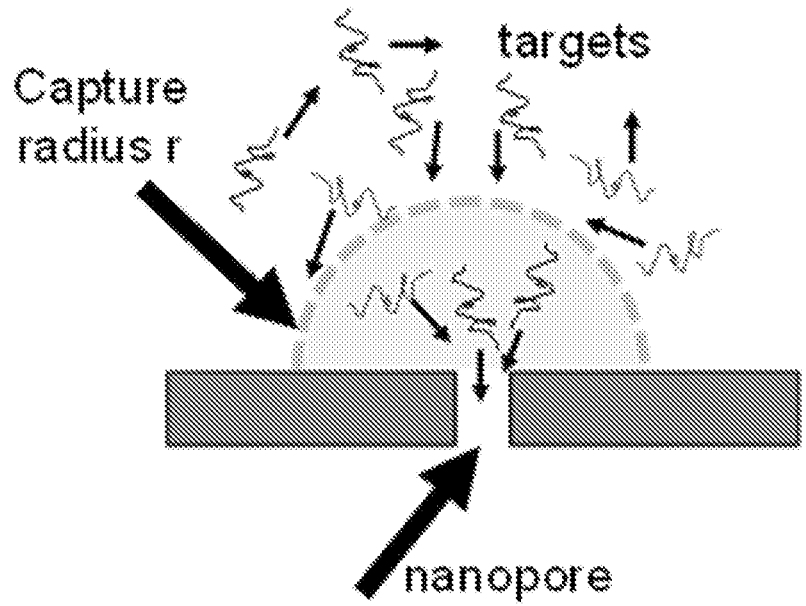
FIG. 2B is an illustration of the concept of a capture volume around a nanopore in which target molecules experience a sufficiently strong electric force that they move through the pore.

FIG. 2A illustrates the principle of nanopore-based molecular analysis. Two chambers are separated by a membrane that contains a nanoscopic opening—the nanopore. Ionic current flowing between the two chambers is modulated if a particle passes through and at least partially obstructs the opening. In the bottom panel of FIG. 2A, a reduction in current (blockade) is shown, but increased current can also be observed depending on factors related to the nanopore, the charge, and the analyte passing through the pore [47]. As described herein, a "blockade" means any measurable change in current upon particle translocation through the nanopore.

This detection principle was first demonstrated using "biological" pores (e.g. α-hemolysin proteins embedded in a lipid membrane) [21,33]. Over the last 15 years, "solid-state" pores have been created in inorganic membranes using various nanofabrication techniques. Solid-state pores are more robust than their biological counterparts and can be fabricated with different diameters that can be adapted to a wide range of target sizes from single DNAs to large nanospheres [48-51]. They can also readily be integrated with microfluidic channels for efficient, large-scale sample manipulation.

FIG. 2B illustrates the concept of the nanopore capture radius r that defines a volume around the pore in which target particles are exposed to a sufficiently strong electric field that they are pulled into and through the nanopore. This radius determines the target capture rate R which is given by $$R = 2\pi \cdot C \cdot D \cdot r \quad (1)$$

Where C is the concentration and D is the diffusion coefficient of the target molecule. For typical experimental conditions, the capture radius is only a few micrometers large. This accounts for the present limitations of nanopore capture for applications in medical diagnostics where starting concentrations of target molecules in biological fluids can be in the attomolar to femtomolar range ($10^3$-$10^6$ targets/mL or less concentrated depending on the volume around the pore) [11,52-56].

DNA targets (with a diffusion coefficient of about ~1 $\mu m^2/s$) at a concentration typical for infectious diseases ($10^3$/mL) [52-56] would translocate at a rate of $2 \cdot 10^{-8}$/s through a nanopore with a 3 μm capture radius. It would, therefore, essentially take effectively forever to detect even a small fraction of the 10,000 targets contained in 10 mL of serum. However, if all 10,000 targets were positioned within a cube of 10 μm edge length around the pore, the translocation rate would be 188/s and all targets would be detected in less than one minute (53 s).

There is an enormous mismatch between a nanopore's capture volume (~50 fL) and the sample volume needed to detect a sufficient number of target molecules for a typical molecular diagnostic test (~10 μL-10 mL). Some potential solutions could include forcing all sample liquid through the nanopore(s) or using a massive number of nanopores in parallel. Such solutions face difficult to surmount challenges involving fluid transport through nanoscale channels (e.g. too high of pressure for the nanopore/membrane to retain integrity and clogging of the nanopores) and the need for complex electronic circuitry.

The capture rate of a nanopore can be enhanced by a variety of methods, including salt gradients to tailor a specific voltage drop around the nanopore [41], the modification of internal charge in a-HL protein pores [42,43], and pressure gradients [44]. Enhancement factors between 10 and 80 can be observed using such methods, with the best results from dielectrophoretic trapping of DNAs at the tip of a nanopipette using alternating DC and AC fields [45]. Any or all of these can be used in combination with the disclosed devices, systems, and methods.

Incorporation of Nanopores with the Optofluidic Platform

Figure 4A:
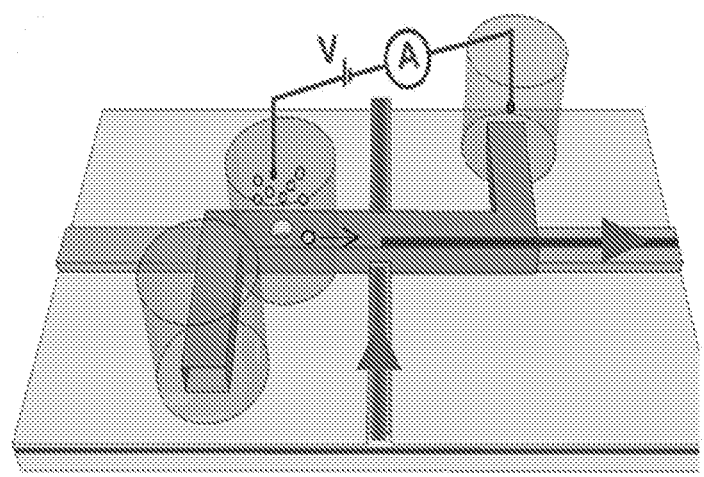
FIG. 4A is a drawing showing a schematic view of nanopore placement and applied voltage to effect particle translocations into fluidic channel.
Figure 4B:
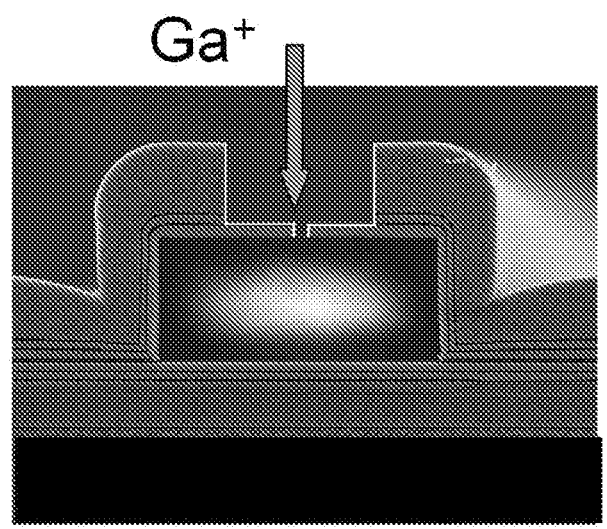
FIG. 4B is an image showing nanopore integration via combination of wide micropore and ion-beam milled nanopore in thin nitride or oxide membrane above channel.
Figure 4C:
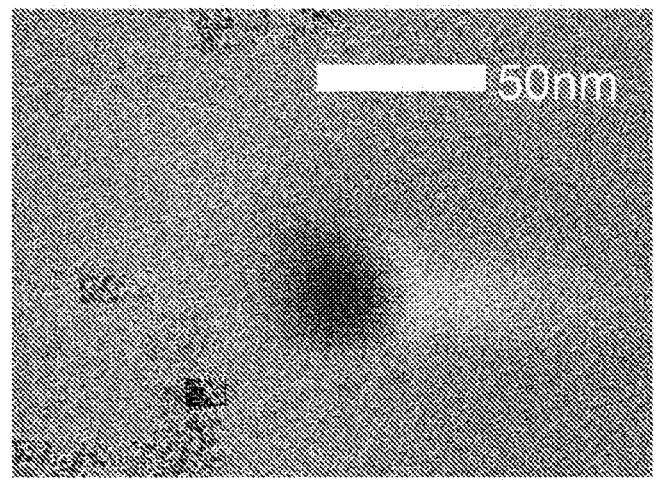
FIG. 4C is a top-down view of 20 nm nanopore used for single-molecule DNA detection [68].
Figure 4D:
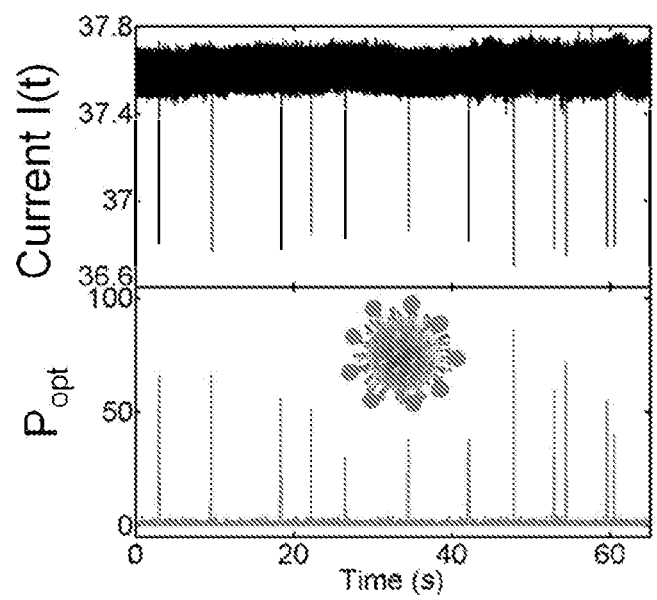
FIG. 4D is a trace showing detection of individual labeled H1N1 viruses on an optofluidic chip [67,69].

Nanopores can be incorporated into an optofluidic platform resulting in both the electrical and optical detection of single biomolecules. This has been demonstrated using H1N1 viruses and DNAs [67-69]. FIG. 4A shows how a third fluidic reservoir can be incorporated over a nanopore in the chip layout of FIG. 3A. Translocation into the fluidic channel is induced and detected by applying a voltage as shown and, once in the channel, a particle can be detected optically using the intersecting waveguide approach. Nanopores can be defined into the top layers of the liquid-core waveguide channel using RIE etching [81,82] or ion milling of a larger micropore, followed by ion milling of a nanopore in a remaining thin membrane (FIG. 4B). The pore size can be controlled by subsequent electron or ion beam exposure [83]. An example of a 20 nm diameter pore is shown in FIG. 4C. FIG. 4D shows simultaneous and correlated electrical (black trace, top) and optical (red trace, bottom) detection of individual, labeled H1N1 viruses on this chip, illustrating the use of the nanopore as a "smart gate" for particle delivery and optical detection on a chip [67-69].

Example—Detection of Zika Virus

A prime example of a disease that could benefit from detection using the disclosed systems and methods is Zika virus (ZIKV) infection. ZIKV RNAs can be detected during the first 1-2 weeks following infection while ZIKV protein can be detected for many months post infection [6-9]. ZIKV presents particular challenges as viremia is generally low and protein biomarkers exhibit cross-reactivity with Dengue infection [9-12]. Thus, a test that detects ZIKV using the disclosed systems and methods is needed.

Disclosed herein is a proposed set of experiments intended to measure both nucleic acid and protein biomarkers in different bodily fluids for investigation of Zika virus (ZIKV) infection using a recently developed marmoset animal model [8,46]. In particular, the disclosed optofluidic based nanopore system is used to detect both nucleic acid and protein targets of ZIKV infection starting from different bodily fluids at clinically relevant concentrations.

Figure 5A:
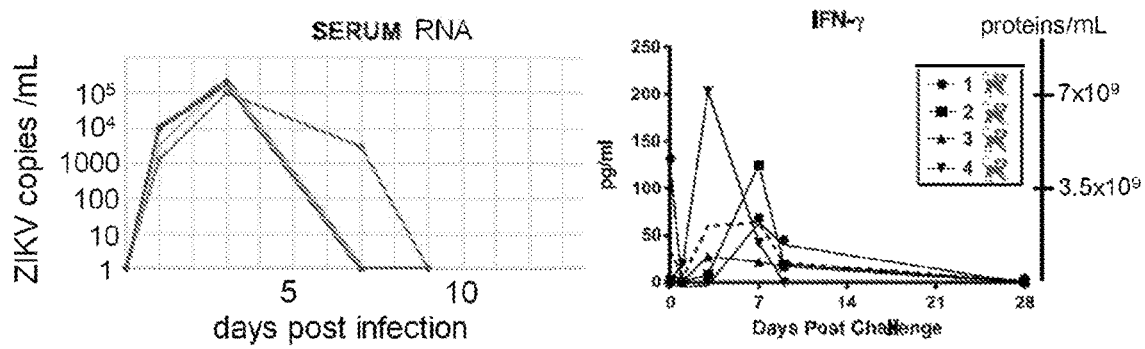
FIG. 5A is a set of two plots showing viral RNA and interferon protein loads in marmosets during ZIKV infection [8].

The 2015 outbreak of Zika virus infection has drawn massive attention to this disease. While the acute epidemic has subsided, many concerns remain, in particular due to the virus' ability to cause severe birth defects [84-86]. A model is available, showing that ZIKV infection in marmosets closely resembles human illness [8]. In both humans and marmosets, both nucleic acid and protein biomarkers should be used for detection as the protein biomarkers and nucleic acid biomarkers appear during different disease stages [6,7, 52]. Immunoassays have difficulty in detecting Zika virus due to pronounced cross-reactivity of Zika antibodies with other flaviviruses, in particular Dengue virus [10,11]. FIG. 5A shows that both biomarker loads in marmosets are well within the range previously detected on a chip-based platform [65]. Similar levels are found in humans [11,52,86].

Figure 5B:
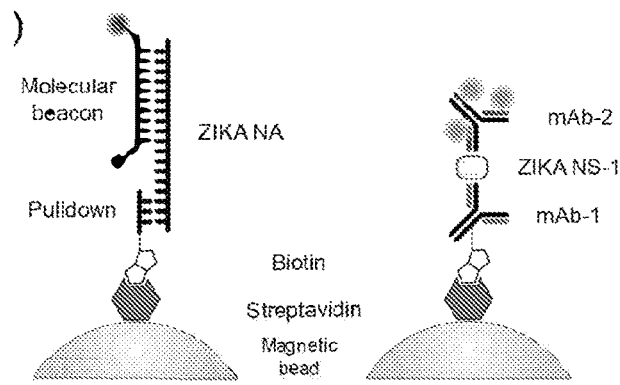
FIG. 5B is a depiction of bead-based constructs for solid-phase extraction of Zika nucleic acid and protein biomarkers.
Figure 5C:
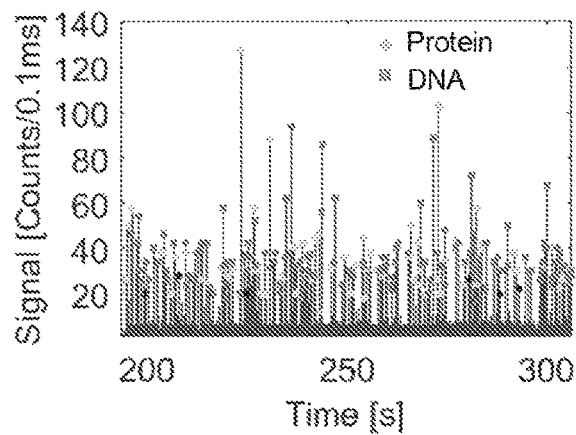
FIG. 5C is a plot showing results from spectrally multiplexed optical detection of the beads depicted in FIG. 5B with attached target molecules and labels on optofluidic platform.

If both biomarker types are to be detected reliably, repeatedly, and in a number of sample matrices (blood, saliva, urine, semen [8]), an instrument that can detect both biomarker types using small starting volumes is essential. Disclosed herein is the development and validation of a solid-phase assay for specific extraction of both nucleic acids and NS-1 protein specific to Zika infection. These constructs are schematically depicted in FIG. 5B. Both target types were successfully bound to streptavidin-functionalized microbeads with excellent specificity. Note that each bead holds many (up to 240,000) targets. This approach was validated in a fluorescence-based assay where fluorescent labels with different spectral response were bound to the extracted targets as shown [87]. Successful binding was shown (FIG. 5C) using multiplex fluorescence detection on the optofluidic chip as previously demonstrated for nucleic acids and virus particles [65,66].

Label Free Detection of Zika Virus Using the Disclosed Systems and Methods

The disclosed project can take advantage of the specificity and universality of bead-based solid-phase extraction described in the previous example. However, the analysis can be simplified significantly by replacing optical detection of a complex sandwich construct with label-free electrical nanopore detection with optimized throughput.

The approach can enable molecular diagnostics using nanopore detection with high throughput using an integrated platform that combines advanced sample preparation with individual molecule electrical detection. Three specific areas can be addressed: nanopore capture rate enhancement using optical trapping of carrier beads; integration of microfluidic sample processing for high throughput molecular detection at ultralow (attomolar) concentrations; and multiplex analysis of nucleic acids and proteins for ZIKV infection starting from complex sample matrices (serum, saliva, urine, semen) using a marmoset animal model.

There are two elements that can enable nanopore detection with high throughput at low target concentrations that are meaningful for molecular diagnostics: One is to bring and hold the target molecules close to the capture volume of the nanopore using the optical trapping of carrier microbeads. This results in efficient capture by the pore, and thus rapid detection of the target molecules.

The second element is the selection and preconcentration of target molecules onto the carrier microbeads. This element ensures the specificity of the assay and that a low limit of detection (LoD) down to attomolar concentrations can be reached using nanopore detection.

The third element is to validate the platform with target analytes contained in a complex sample matrix. To demonstrate this, new high-throughput nanopore analysis can be used for nucleic acid and protein detection of ZIKV infection in several relevant fluids. These results of this project would be applicable to a broad range of diseases and biomarker types.

Nanopore Capture Rate Enhancement Using Optical Trapping of Carrier Beads

Figure 7A:
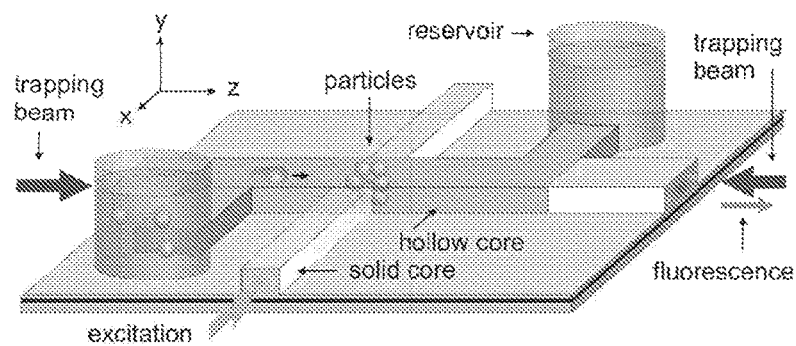
FIG. 7A is a schematic of optical particle trapping on an optofluidic chip using counter-propagating beams (purple) [90].

The delivery of target molecules loaded on microbeads to a nanopore is based on integrated optical particle trapping using liquid-core waveguide microchannels [88-92]. FIG. 7A shows schematically how the generic optofluidic chip of FIG. 3A can be turned into a particle trap. Two laser beams are coupled into the chip from opposite ends (purple arrows). The laser beams exert optical forces on microparticles in the channel: The gradient force pulls particles to the center of the channel where the intensity is highest, and the scattering force pushes them along the beam direction [88,89]. The two beams produce opposing scattering forces, and, because each beam experiences some propagation loss, there is one point in the channel at which these forces balance out and the particle is trapped [90]. The position of the trapping point can be controlled by adjusting the relative power in the two trapping beams [90].

Figure 7B:
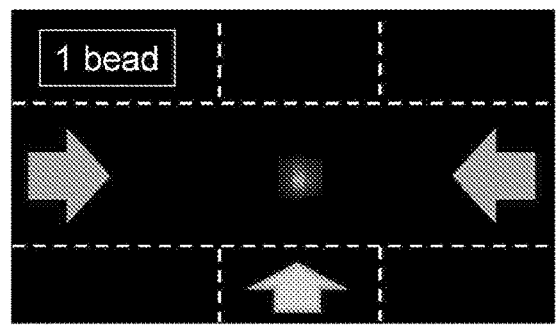
FIG. 7B is the trapping of a single fluorescent microbead using the trap depicted in FIG. 7A.
Figure 7C:
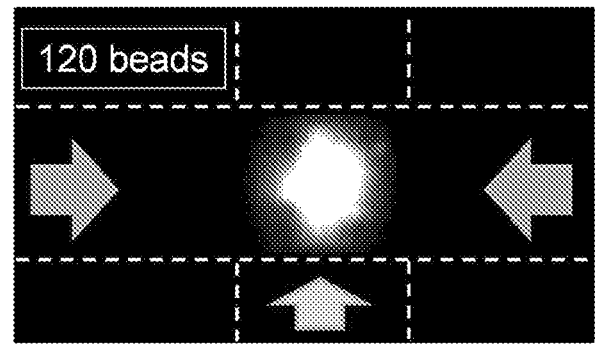
FIG. 7C is the trapping of approximately 120 fluorescent microbeads using the trap depicted in FIG. 7A. For both FIGS. 7B and 7C, the beads are visualized by using excitation fluorescence with a crossing waveguide (green arrow) as described in [90 and 91].

Another important advantage of this trap in the context of this proposal is that many particles can be optically "collected" to create significant local concentration enhancement [91]. FIGS. 7B and 7C show top-down images of an individual and over 120 fluorescent microbeads, respectively. These beads were trapped at the intersection between the liquid channel and the crossing solid-core waveguide and were visualized by exciting fluorescence with a crossing beam as illustrated in FIG. 7A.

Figure 8A:
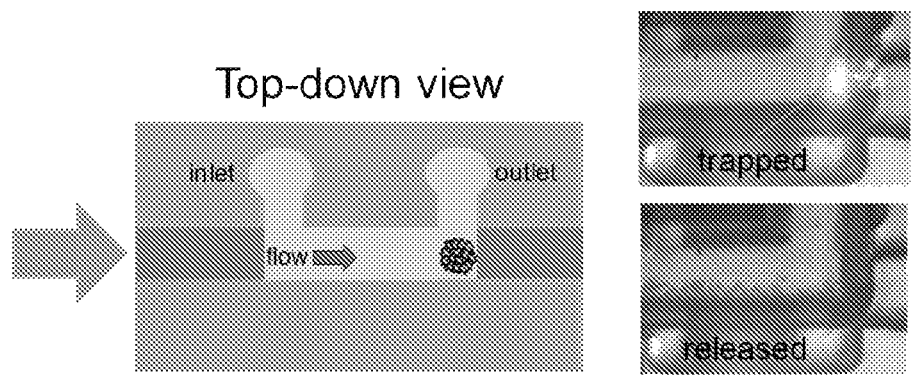
FIG. 8A (left panel) is a top-down view of optofluidic chip: a laser beam guided through a channel (trapping beam) traps microbeads against channel wall; top right image: 250 fluorescent beads trapped using the trapping beam; bottom right image: beads were released without clogging by turning off the trapping beam.
Figure 8B:
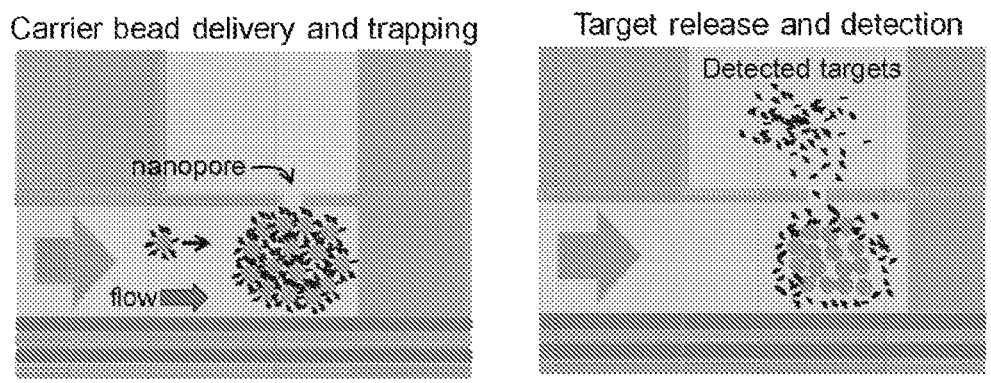
FIG. 8B is a side view of an optofluidic chip with a nanopore over the trapping location; targets are then released from beads within the capture radius of pore and detected using the nanopore.

Optical manipulation of microbeads on a chip can be used to deliver molecular targets to a nanopore for detection. FIG. 8 shows one example of an approach that significantly simplifies the optical arrangement of FIG. 7A. First, FIG. 8A shows a top-down view of the chip where a single laser beam is used to push/trap a collection of target-carrying microbeads against the channel wall. The two camera images in FIG. 8A show successful trapping of 250 fluorescent microbeads in the presence of the beam (top), and successful release without sticking to the wall and clogging the channel (bottom). Using this much simpler trapping method, nanopore detection can be performed as follows: FIG. 8B shows a side view of the area of interest where the fluidic channel containing target-carrying microbeads sits on top of an ARROW layer stack for optical confinement

[60-66]. The microbeads are brought into the central waveguide region from reservoirs using pressure-based flow (see FIG. 8A) and assembled in the trap directly under the nanopore. Using a suitable mechanism (addition of heat, change in pH, etc.), the targets can be released from the beads and electrophoretically pulled through the pore (FIG. 8A, right) at a high rate due to their proximity to the nanopore capture volume. Note that this approach allows the analysis of several batches of beads in rapid succession by turning off the trapping beams, flushing the channel of beads, then filling the trap again with a new set of beads.

The feasibility of this approach has been shown to detect both nucleic acids and proteins. For nucleic acids, magnetic microbeads (1 urn diameter) were functionalized with 14-bp pulldown oligomers that matched the sequence of a mutated melanoma gene (BRAFV600E). This construct had previously been validated in an optical detection assay [80]. Matching 100-mer synthetic targets were then added to the beads to form the construct shown in the inset of FIG. 9A.

Nucleic Acid Detection

Figure 9A:
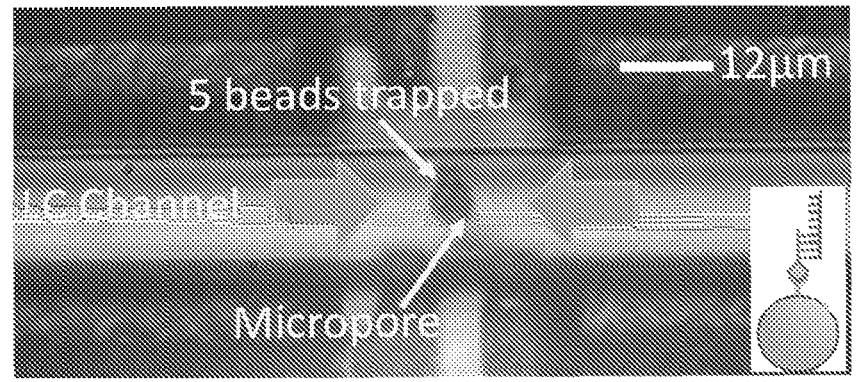
FIG. 9A is an image of trapping region with 5 beads trapped under a micro nanopore; the inset shows the bead functionalized with the DNA construct for capture. The pulldown oligo is complexed with the bead, while the target molecule is hybridized to the pulldown molecule.

The dual-beam trap of FIG. 7A was then used to trap the target-bead complexes and position them under a micro/nanopore. FIG. 9A shows an image of 5 beads (monitored by video camera) collected under the micropore (the 20 nm nanopore is not resolved). After the beads were trapped, the chip was heated above the melting temperature (34° C.) of the target nucleic acid to the pulldown sequence and a voltage was applied across the pore to detect the released nucleic acids.

Figure 9B:
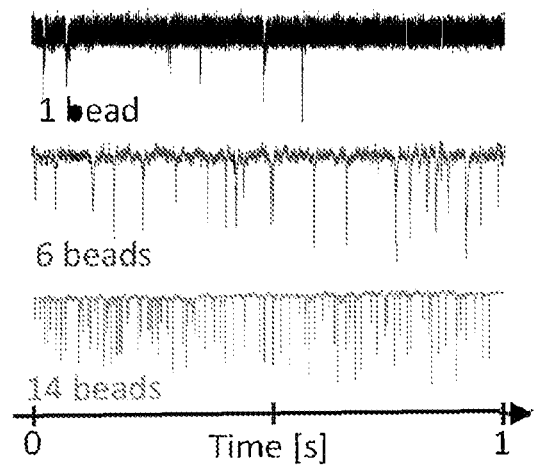
FIG. 9B shows the time-dependent current across nanopore after the release of the target molecule. Target molecules were released using heat.
Figure 9C:
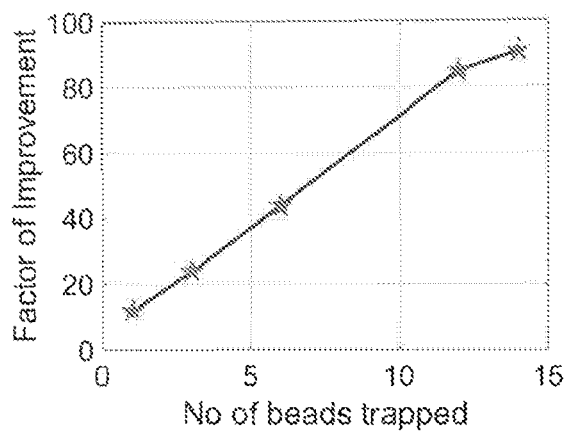
FIG. 9C is a plot depicting the capture rate improvement as a function of the number of trapped beads (relative to unconcentrated bulk solution).

FIG. 9B shows the observed translocations of the target nucleic acids across the nanopore at the indicated number of trapped beads. The translocation rate correlates with number of beads indicating that target nucleic acids are concentrated near the pore when more beads are concentrated near the pore. The measured translocation rates were compared to the translation rate of a non-concentrated bulk solution where 240,000 target molecules (the same number of targets as there are binding sites on a single bead) are uniformly distributed throughout the fluidic channel (i.e. without beads at a 2 nM concentration). FIG. 9C shows the improvement factor in the translocation rate compared to the non-concentrated bulk concentration as a function of the number of trapped beads. The disclosed system and method results in an improvement in translocation rate between one and two orders of magnitude with a nearly linear dependence on the number of beads trapped.

The amount of improvement is limited by two main factors. First, it is likely that not all binding sites on the bead were occupied. Second, the assay was limited by the experimental setup where two minutes passed between turning off the particle trap, turning on the heater and starting the electrical nanopore detection. During this time, the targets diffused away from the pore by a distance of up to ~220 µm as illustrated in FIG. 8D. The observed improvement was in excellent agreement with an estimate based on the diffusion of the target molecule between the release of the particles and the starting of the nanopore detection. Further optimization of the system and methods could result in more efficient target detection.

Protein Detection

Figure 10A:
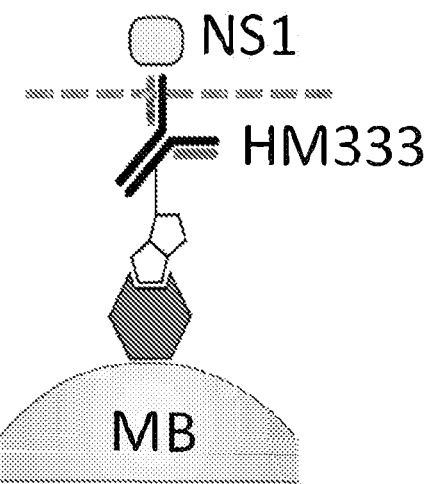
FIG. 10A illustrates construct for nanopore-based detection of Zika NS-1 protein.
Figure 10B:
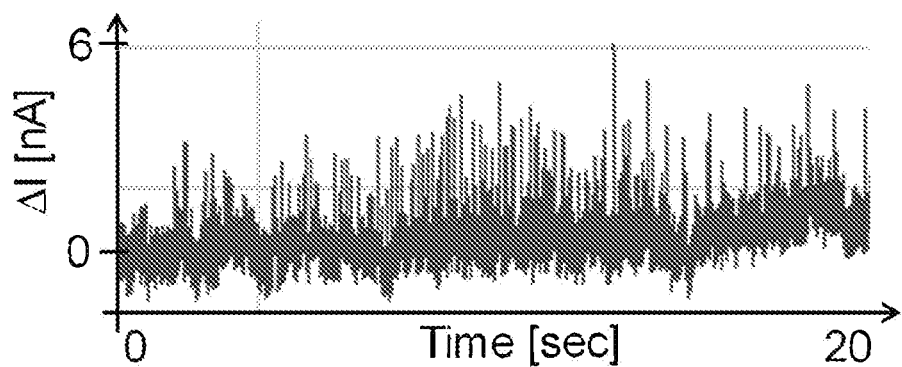
FIG. 10B is a graph showing partial segment observation of current blockades after thermal NS-1 target release off chip.

Protein detection used a version of the solid-phase extraction construct of the optical assay shown in FIG. 5B. The protein detection version of the construct is shown in FIG. 10A. After incubation of NS-1 proteins with beads functionalized with the anti-NS-1 antibody 1-11M333, the beads were secured with a magnet so that unbound target molecules were removed from solution. Target molecules were released from the beads by heating the solution to 50° C. and the supernatant was collected. To this point, sample preparation using this construct has been performed off chip, but can be moved on-chip without undue experimentation. Supernatant was introduced into the optofluidic chip and a voltage applied across the nanopore. FIG. 9B shows the detection of NS1 in the nanopore. In particular, NS1 protein molecules block the current across the 20 nm nanopore due to its size (~2 nm×9 nm) [93]. This demonstrates that the disclosed methods and system can be applied to multiple target molecules. FIG. 9C shows the scatter plot of blockade depth and duration for all 4,652 blockade events that were detected. The values are clearly distinct from those of HM333 antibodies, confirming that the NS1 antigen is being detected.

Figure 9D:
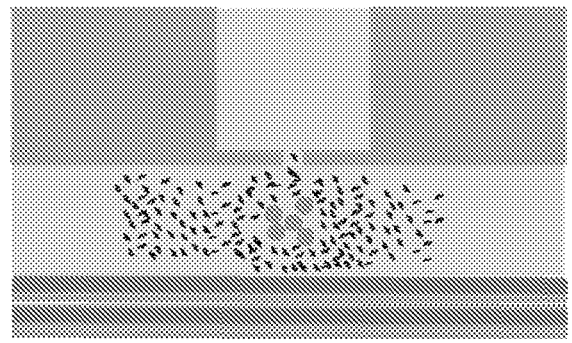
FIG. 9D is a schematic view of partial diffusive target dispersion as result of delay between release of the targets from the beads and nanopore detection.

Example—Demonstration of Million Fold Capture Rate Enhancement Using Optical Trapping Optimization of the disclosed process will involve demonstrating analyte detection using the simpler single-beam mechanism of FIG. 8A which requires less optical power and offers easier balancing of optical and flow pressures. It will also involve improving the capture enhancement by (i) trapping in excess of 1,000 beads (instead of ~10 as shown in FIG. 9A), and (ii) optimizing conditions to allow simultaneous target release and electrical readout. This will eliminate the time delay before detection (shown in FIG. 9D). The optimization can be accomplished by electrical isolation of nanopore readout with respect to the optical trapping and heating components. Additionally, nanopore shape can be optimized in combination with the applied voltage to create an electrical capture volume that matches the bead trapping region as much as possible. This field profile optimization can be done using COMSOL simulation which has been shown to model different nanopore shapes [67-69,83]. Nucleic acids (BRAF-V600E oligomers) can then be used to demonstrate a capture rate enhancement compared to bulk solution detection of 1,000,000×—four orders of magnitude higher than previously reported enhancements [45].

FIGS. 8 and 9 show that trapping-based capture rate enhancement is feasible. However, if the method is ultimately limited by electrical crosstalk, a purely flow-based implementation of the single-beam method that pushes the beads against an obstruction in a straight channel can be used in lieu of optical trapping. Nanofluidic filtering structures that can be used in the purely flow-based implementation are described in, for example, [94].

Example—Nanopore Detection of Nucleic Acid and Protein Targets from the Same Sample Bead-based target delivery for nanopore-based molecular analysis has been selected as an exemplary approach because microbead-based solid-phase extraction (SPE) has been successfully used for isolation of different analyte types [64,65,95-99]. The results in FIGS. 8A-10C can be expanded upon to demonstrate electrical detection of both nucleic acid and protein Zika targets with enhanced capture rate. Nanopore detection of the Zika nucleic acids (synthetic oligomers) from bulk solution, can be demonstrated similar to the NS-1 detection demonstrated above. These results provide a reference for blockade signals and unenhanced rates for both targets. Trapping-enhanced detection of both nucleic acids and proteins on chip can be achieved using the proposed single-beam trapping (FIG. 8A). Capture rate improvements for each target type will be measured and optimized separately. From these measurements, the target release method (thermal, pH, photocleaving etc.) can be optimized as described in [96-99,100-102]. Additional conditions can be further optimized, for example, by maximizing the strength of all bonds relative to the target-pulldown connection and optimizing the pulldown sequence design for a desired melting temperature (for nucleic acids).

The disclosed results show that bead-based extraction for both targets is possible and that both proteins and nucleic acids can be released from the beads using moderate thermal activation. While thermal release has been the method of choice for nucleic acid assays, it may not prove optimal for protein release. If thermal release is too slow or inefficient, other methods such as photo-cleaving, changing the pH or the salt concentration (while the beads remain trapped) can be used [96-99,100-102]. Care will be taken with the latter approach since the salt concentration also affects the details of the electrical nanopore detection process. Secondly, while this does not appear to be an issue in the disclosed results, if current blockade signals from either target are too small, nanopore diameter and thickness can be optimized as can the binding of a larger entity (e.g. longer nucleic acid, or secondary antibody) to the target before release from the bead. In that case, the additional entity will be read out by the pore, but specificity is maintained as its presence relies on prior binding of the target as in a standard sandwich assay (see e.g. FIG. 10A).

Example—Limit of Detection (LoD) and Dynamic Range (DR) for Nucleic Acids and Proteins The disclosed systems and methods must detect clinically relevant ranges of analytes—competitive with current gold standard methods. RNA loads for ZIKV infection range from 103-106/mL [11,52,53,103]. NS1 concentrations are on the order of 109/mL, but the dynamic range is not well investigated due to the limited range of ELISA assays [104]. The optofluidic chips used in the disclosed systems and methods have demonstrated low LoDs and record DRs using an optical readout [65]. These assay parameters can be assessed systematically for electrical nanopore detection using serial dilutions of nucleic acid and protein samples. LoD and DR will be determined individually at first, and finally for dual detection from a single sample containing both targets. Optimization, e.g. target pre-concentration can be done with synthetic targets in buffer solution, In the final stage of the project, both parameters will be assessed in clinical samples.

Figure 11A:
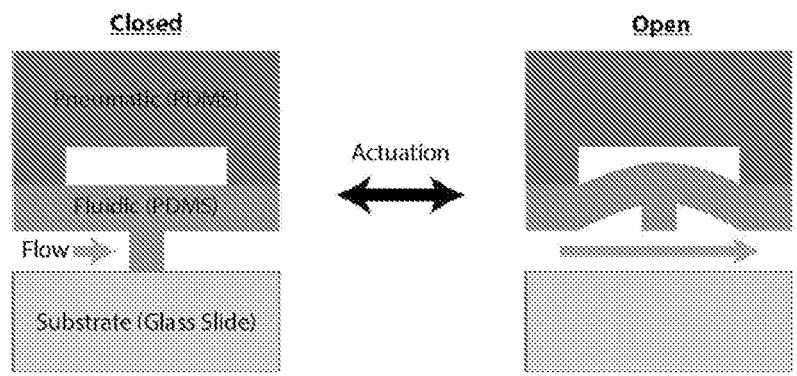
FIG. 11A illustrates the operational principle of lifting-gate microvalve [88,89].
Figure 11B:
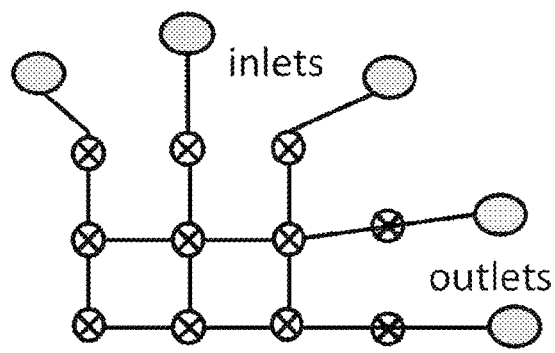
FIG. 11B illustrates an example arrangement of microvalves into an interconnected network ("automaton") with 0.1-μL operating volume per valve.
Figure 11C:
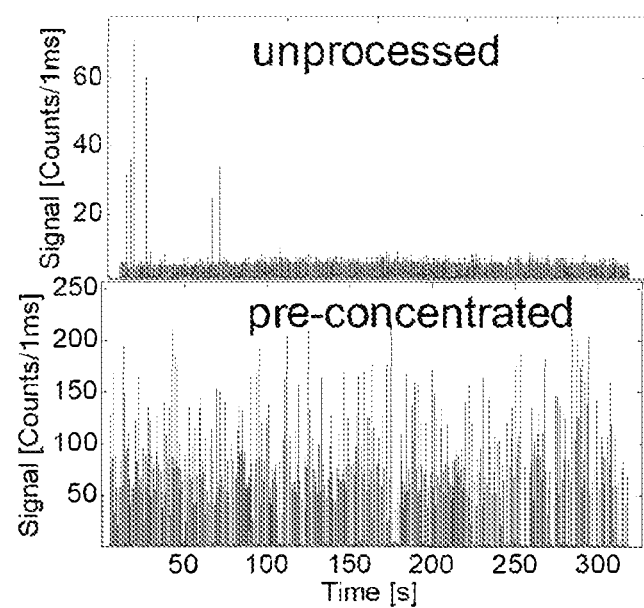
FIG. 11C is a graph showing the results when the automaton of FIG. 11B is used for DNA pre-concentration onto magnetic beads [65]. Fluorescently labeled targets were concentrated by 335× from 3 mL into a test volume of 5 μL for dramatic increase in optical detection rate.

Example—Integration of Microfluidic Sample Processing for High Throughput Molecular Detection at Ultralow (Attomolar) Concentrations A higher capture rate at the nanopore location is important for detection. Similarly, it is important to bind target molecules to the carrier beads with high specificity, and from very low starting concentrations. One approach that can be used is described in references [64,65,78,80]. The approach is based on arrays of interconnected lifting-gate microvalves [105-107] whose operating principle is shown in FIG. 11A. The valves include three layers with a thin flexible PDMS membrane in the center separating pneumatic and sample-carrying microchannels. As long as no negative pressure is applied in the pneumatic layer, the valve seat sits on the substrate and prevents fluid from passing in the fluidic layer. With negative pressure, the valve is raised and fluid can pass (right image in FIG. 11A). FIG. 11B shows how valves with cross-shaped valve seats can be arranged into networks ("automata") that can carry out complex sample preparation tasks by operating the valves in proper sequence [64,65,78,106,107].

Figure 3B:
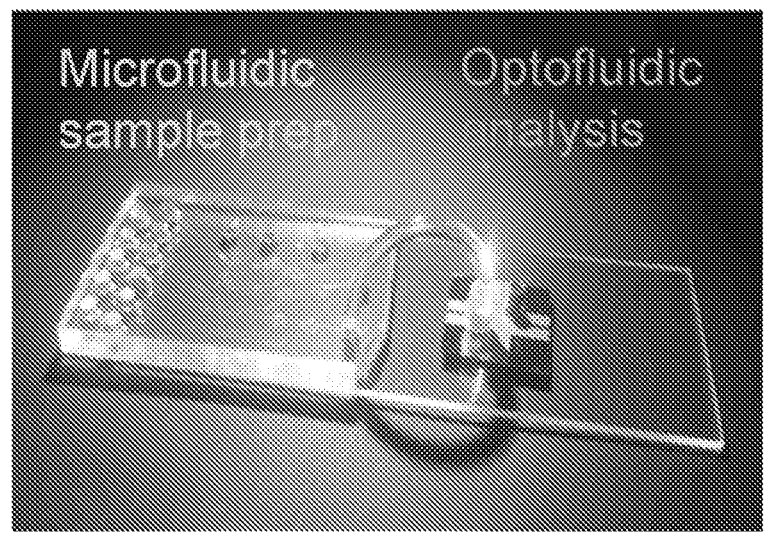
FIG. 3B is an image of a hybrid optofluidic system that combines sample preparation and analysis [65].
Figure 3C:
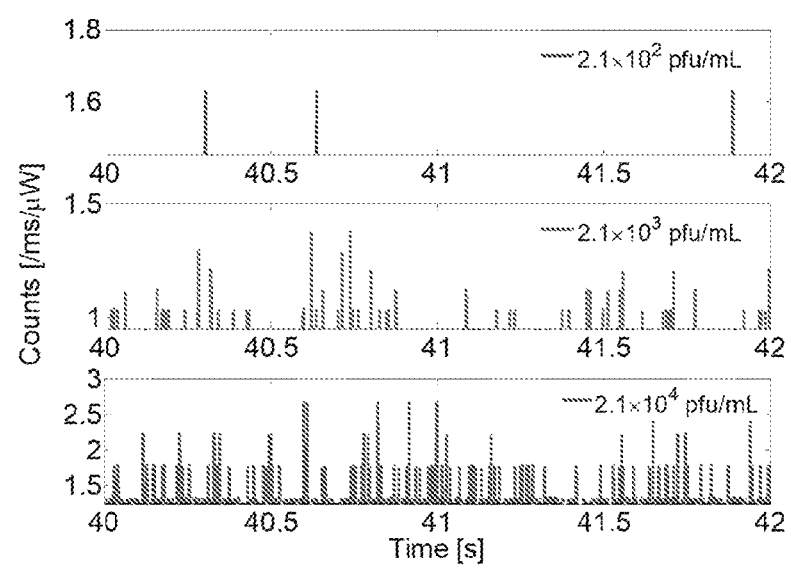
FIG. 3C is a graph showing concentration dependent amplification free detection of Ebola virus RNA's using the optofluidic chips of FIGS. 3A and 3B [65].
Figure 10C:
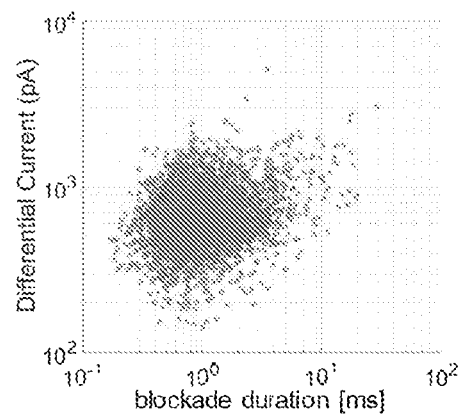
FIG. 10C is a scatter plot of 4,652 translocation events.

These automata have been used to successfully implement on-chip sample prep steps for amplification-free Ebola detection (see FIGS. 3B and 3C) [65]. The automaton microvalve architecture allowed for target pre-concentration by collecting magnetic beads from a large starting volume in a single 100 nL microvalve, followed by resuspension and target release in a much smaller volume. FIG. 10C illustrates this principle as beads containing synthetic Ebola sequences tagged with molecular beacons (analogous to FIG. 10A) that were concentrated in an automaton valve by 335× from 3 mL to 5 μL [65]. Using this principle, an ultralow limit of detection of 103/mL (1.7 aM) for Ebola RNA detection has been demonstrated. This corresponds to the low end of the clinically relevant range [55]. The automaton chips can be used for sample preparation starting from whole blood [80].

Automaton chips can be used to implement the extraction of specific Zika nucleic acids (both synthetic oligomers and whole genomes) and proteins (NS-1). Protein and nucleic acid targets can be assessed individually using the previously described automaton layout [64,65]. Solid-phase extraction, followed by nanopore detection can be used to detect a series of starting concentrations of target molecules in buffer solution. Serial dilutions of these target molecules can cover the concentration range from 109/mL (1.7 pM) to 103/mL (1.7 aM) for nucleic acids and 10 nM to 10 fM for proteins, respectively. Targets can be mixed on chip with 100-1,000 functionalized microbeads to be trapped subsequently in the optofluidic chip for nanopore readout. Translocation rates can be recorded in triplicate for each starting concentration.

These capabilities will be demonstrated with progressively more complex sample matrices: Nanopore-based detection of both molecular targets with starting concentrations of 103/mL (nucleic acids) and 107/mL (proteins) will first be achieved. After successfully reaching this limit for each target individually, on-chip extraction of both targets from a mixed buffer solution will be implemented. To this end, nucleic acid and protein beads can be stored in different microvalves for sequential extraction on the chip. For all experiments, negative controls without any and with non-matching targets can be run. Successful sample preparation will also independently be confirmed by fluorescent labeling of the targets (see FIG. 5) and fluorescence detection on a standard ARROW optofluidic chip [80], i.e. without the nanopore detection. Note that an important advantage of the disclosed approach is that the details of the blockade signal are not important for target identification since target specificity is provided by the bead extraction step. Finally, sample preparation will be done using biological samples from marmosets such as cell supernatants, serum, saliva, semen, or urine.

Target-specific pulldown onto beads and preconcentration has successfully been used [64,65,95-99]. There are two possible complications in the optimization of this process. If the extraction of ~10,000 target molecules (10 mL volume at 103/mL concentration) is too inefficient, then several approaches can be used to improve the efficiency. A smaller microvalve volume can be used for incubation and mixing. Alternatively, a more efficient "bubble mixing" automaton chip can be used [78,79]. This chip features large incubation reservoirs that hold the magnetic beads for target extraction. Air bubbles are periodically pushed through these reservoirs to enhance particle mixing and target extraction. Target extraction can be optimized using labeled synthetic Ebola oligomers as test targets. Each wafer can hold 64 such incubation areas, enabling rapid (~1 hr) processing of large starting volumes [78]. Another alternative involves a two-step process in which targets are first pulled down onto a large number of beads (~106), then released into a small automaton valve volume. This release is followed by transfer to and rebinding onto the desired final small number of beads. Still another alternative involves leaving the targets on a larger number of beads (103-104) and testing these sequentially on the optofluidic chip in batches of ~100 as the detection step is rapid and can be parallelized.

Another possible complication involves the loss of targets during on-chip sample preparation due to inefficient pull-down onto the beads and attachment to the microchannel and microvalve walls. To minimize these loss mechanisms, glass channels can be coated with polyethylene glycol compounds [108-110], while bovine serum albumin (BSA), poly(l-lactic acid) or other materials can be applied to PDMS chips. The coatings can be optimized until the target limit of detection has been reached. It should be noted that the disclosed approach to deliver carrier beads in an optical beam has the advantage of keeping the target molecules away from the wall on the optofluidic chip during transport to the trapping point [88].

Figure 6:
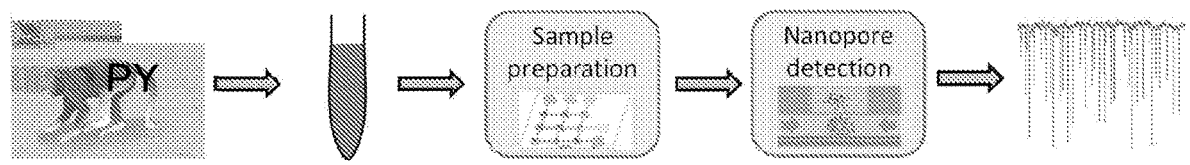
FIG. 6 illustrates the elements of a lab-on-chip system for molecular analysis.

Example—Multiplex Direct Detection of ZIKV Infection Starting from Complex Sample Matrices The disclosed systems and methods can be tested for their ability to handle complex starting matrices that include target molecules (see FIG. 6). Zika infection is ideally suited as a test case because four different sample types (serum, saliva, semen, urine) are relevant for disease detection and monitoring [8,11,52,53,99,103]. Validation can be performed in two phases. In the first phase, the target molecules will be detected in cell supernatant, and in the second phase they will be detected in samples comprising the four sample types listed above. Off-chip sample preparation can be initially used to measure nucleic acid and protein levels on the nanopore chip. LoD and dynamic range can be assessed with the goal of reaching the same performance as for the initial buffer-based tests. Later, the series can be repeated using the automaton chip for sample preparation and the nanopore chip for detection. Again, performance for LoD and DR will be quantified by using serial dilutions of all sample types. Measurement of target molecules in each of the listed sample types has been performed on an optofluidic platform [65,80]. Optimization of can involve surface treatment of the microchannels, which can include surface treatments that are described herein and known in the art.

REFERENCES

All of the following are incorporated by reference in their entirety.
1] Hamburg, M. A. and Francis S. Collins, F. S., "The Path to Personalized Medicine", *N. Engl. J. Med* 363, 301-304 (2010).
[2] Ziegler, A., Koch, A., Krockenberger, K. And Grosshennig, A., "Personalized medicine using DNA biomarkers: a review", *Hum. Genet.* 131, 1627-1638 (2012).
[3] Ashley, E. A., "Towards precision medicine", *Nature Reviews Genetics* 17, 507-522 (2016).
[4] Gonzalez-Garay, M. L. "The road from next-generation sequencing to personalized medicine", *Per Med.* 11, 523-544 (2014).
[5] Frei, A. P., Bava, F., Zunder, E. R., Hsieh, E. W. Y., Chen, S., Nolan, G. P., and Gherardini, P. F., "Highly multiplexed simultaneous detection of RNAs and proteins in single cells", *Nature Methods* 13, 269-275 (2016).
[6] https://www.euroimmun.com/products/indications/infektions-serologie/zika-viruses.html
[7] https://www.euroimmun.com/filead min/zika/pdf/Zika-Serological_differential_diagnosis_ELISA-EUROIMMUN.pdf
[8] Chiu, C. Y., et al., "Experimental Zika virus inoculation in a new world monkey model reproduces key features of the human infection", *Sci. Rep.* 7, 17126 (2017).
[9] Huzly, D., Hanselmann, I., Schmidt-Chanasit, J., and Panning, M., "High specificity of a novel Zika virus ELISA in European patients after exposure to different flaviviruses", *Euro Surveill.* 211, 30203 (2016).
[10] Osterholm, M. T., "Ebola and Zika: Cautionary tales", *Science* 353, 1073 (2016).
[11] Lanciotti, R. S., kosoy, O. L., Laven, J. J., Velez, J. O., Lambert, A. J., Johnson, A. J., Stanfield, S. M., and Duffy, M. R., "Genetic and serologic properties of Zika virus associated with an epidemic, Yap state, Micronesia, 2007", *Emerging Infectious Diseases* 14, 1232-1239 (2008).
[12] Waggoner J. J., and Pinsky B. A., "Zika virus: diagnostics for an emerging pandemic threat", *J. Cin. Microbiol.* 54, 860-867 (2016).
[13] Cornish, P. V., and Ha, T., "A survey of single molecule techniques in chemical biology", *ACS Chem. Biol.* 2, 53-61 (2007).
[14] Schuler, B. and Eaton, W. A., "Protein folding studied by single molecule FRET", *Curr. Opin. Struct. Biol.* 18, 16-26 (2008).
[15] Rhoades, E., Gussakovsky, E., and Haran, G., "Watching proteins fold one molecule at a time", *PNAS* 100, 3197-3202 (2003).
[16] Seisenberger, G., Ried, M. U., Endreg, T., Buening, H., Hallek, M., and Braeuchle, C., "Real-Time Single-Molecule Imaging of the Infection Pathway of an Adeno-Associated Virus", *Science* 294, 1929 (2001).
[17] Chang, M. I., Panorchan, P., Dobrowsky, T. M., Tseng, Y., and Wirtz, D., "Single-Molecule Analysis of Human Immunodeficiency Virus Type 1 gp120-Receptor Interactions in Living Cells", *J Virol.* 79, 14748-14755 (2005).
[18] Bustamante, C., Bryant, Z., and Smith, S. B., "Ten years of tension: single-molecule DNA mechanics", *Nature* 421, 423-427 (2003).
[19] Levene, M. J., Korlach, J., Turner, S., Foquet, M., Craighead, H., and Webb, W. W., "Zero-mode waveguides for single-molecule analysis at high concentrations", *Science* 299, 682, (2003).
[20] Eid J. et al., "Real-time DNA sequencing from single polymerase molecules", *Science* 323, 133-138 (2009).
[21] Kasianowicz, J. J., Brandin, E., Branton, D., and Deamer, D. W., "Characterization of Individual Polynucleotide Molecules Using a Membrane Channel" *PNAS* 93, 13770-13773 (1996).
[22] Clarke, J., Wu, H. C., Jayasinghe, L., Patel, A., Reid, A., and Bayley H., "Continuous base identification for single-molecule nanopore DNA sequencing", *Nature Nanotechnology* 4, 265-270 (2009).
[23] Howard, J., "Molecular motors: structural adaptations to cellular functions", *Nature* 389, 561-567 (1997).
[24] Svoboda, K., Schmidt, C. F., Schnapp, B. J.& Block, S. M., "Direct observation of kinesin stepping by optical trapping interferometry", *Nature* 256, 721-727 (1993).
[25] Finer, J. T., Simmons, R. M.& Spudich, J. A., "Single myosin molecule mechanics: piconewton forces and nanometer step", *Nature* 368, 113-119 (1994).
[26] Meyhofer, E.& Howard, J., "The force generated by a single kinesin molecule against an elastic load", *Proc. Natl Acad Sci.* 92, 574-578 (1995).
[27] Funatsu, T., Harada, Y., Tokunaga, M., Saito, K.& Yanagida, T., "Imaging of single fluorescent molecules and individual ATP turnovers by single myosin molecules in aqueous solution", *Nature* 374, 555-559 (1995).

[28] Wieser, S., and Schutz G. J., "Tracking single molecules in the live cell plasma membrane-Do's and Don't's", *Methods* 46, 131-40 (2008).

[29] Kusumi, A., Ike, H., Nakada, C., Murase, K., and Fujiwara, T., "Single-molecule tracking of membrane molecules: plasma membrane compartmentalization and dynamic assembly of raft-philic signaling molecules", *Semin. Immunol.* 17, 3-21 (2005).

[30] http://www.pacb.com/

[31] https://www.singulex.com/technology-science

[32] http://www.bio-rad.com/en-us/applications-technologies/introduction-digital-per

[33] Branton, D., and Deamer, D. W., "Characterization of nucleic acids by nanopore analysis" *Acc. Chem. Res.* 35, 817-825 (2002).

[34] Branton, D., et al., "The potential and challenges of nanopore sequencing", *Nat. Biotech.* 26, 1146-1153 (2008).

[35] Howorka, S., and Siwy, Z, "Nanopore analytics: sensing of single molecules", *Chem. Soc. Rev.* 38, 2360-2384 (2009).

[36] Feng, Y., Zhang, Y., Ying, C., Wang, D., and Du, C., "Nanopore-based Fourth-generation DNA Sequencing Technology", *Genomics, Proteomics & Bioinformatics* 13, 4-16 (2015).

[37] Deamer, D., Akeson, M., and Branton, D., "Three decades of nanopore sequencing", *Nat. Biotech.* 34, 518-524 (2016).

[38] http://www.thenanoporesite.com/groups--companies.html

[39] Han, A., Creus, M., Schirmann, G., Linder, V., Ward, T. R., de Rooij, N. F., and Staufer, U., "Label-free detection of single protein molecules and protein-protein interactions using synthetic nanopores", *Anal. Chem.* 80, 4651-4658 (2008).

[40] Muthukumar, M., "Theory of capture rate in polymer translocation," *J. Chem. Phys.* 132, 195101 (2010).

[41] Wanunu, M., Morrison, W., Rabin, Y., Grosberg, A. Y., and Meller, A., "Electrostatic focusing of unlabelled DNA into nanoscale pores using a salt gradient," *Nat. Nanotechnol.* 5, 160-165 (2010).

[42] Maglia, G., Restrepo, M. R., Mikhailova, E., and Bayley, H., "Enhanced translocation of single DNA molecules through α-hemolysin nanopores by manipulation of internal charge," *Proc. Natl. Acad Sci.* 105, 50, (2008).

[43] Laszlo, H., Derrington, I. M., Ross, B. C., Brinkerhoff, H., Adey, A., Nova, I. C., Craig, J. M., Langford, K. W., Samson, J. M., Daza, R., Doering, K., Shendure, J., and Gundlach, J. H., "Decoding long nanopore sequencing reads of natural DNA", *Nat. Biotechnol.* 32, 829-833 (2014).

[44] Lu, B., Hoogerheide, D. P., Zhao, Q., Zhang, H., Tang, Z., Yu, D., and Golovchenko, J. A., "Pressure-Controlled Motion of Single Polymers through Solid-State Nanopores," *Nano Lett.* 13, 3048-3052, (2013).

[45] Freedman, K. J., Otto, L. M., Ivanov, A. P., Barik, A., Oh, S. H., and Edel, J. B., "Nanopore sensing at ultra-low concentrations using single-molecule dielectrophoretic trapping," *Nat. Commun.* 7, 10217 (2016).

[46] Carrion, R. Jr, and Patterson J. L., "An Animal Model That Reflects Human Disease: The Common Marmoset (Callithrix jacchus)", *Current Opinions in Virology* 2, 357-62 (2012).

[47] Chang, H., Kosari, F., Andreadakis, G., Alam, M. A., Vasmatzis, G., and Bashir, R., "DNA-Mediated Fluctuations in Ionic Current through Silicon Oxide Nanopore Channels," *Nano Lett.* 4, 8, (2004).

[48] Li, J., Stein, D., McMullan, C., Branton, D., Aziz, M. J., and Golovchenko, J. A., "Ion-beam sculpting at nanometre length scales", *Nature* 412, 166, (2001).

[49] Storm, A. J., et al., "Fabrication of solid-state nanopores with single-nanometre precision", *Nature Mater.* 2, 537-540 (2003).

[50] Dekker, C., "Solid-state nanopores", *Nature Nanotechnology* 2, 209 (2007).

[51] Bacri, L., Oukhaled, A. G., Schiedt, B., Patriarche, G., Bourhis, E., Gierak, J., Pelta, J., and Auvray, L., "Dynamics of Colloids in Single Solid-State Nanopores," *J. Phys. Chem. B* 115, 12, (2011).

[52] Barzon, L., Pacenti, M., Berto, A., Sinigaglia, A., Franchin, E., Lavezzo, E., Brugnaro, P., and Palu, G., "Isolation of infectious Zika virus from saliva and prolonged viral shedding in a traveler returning from the Dominican Republic to Italy, January 2016", *Euro Surveill.* 21, 30159 (2016).

[53] Gourinat, A., O'Connor, O., Calvez, E., Goarant, C., and Dupont-Rouzeyrol, M., "Detection of Zika virus in urine", *Emerging Infectious Diseases* 21, 84-86 (2015).

[54] Watzinger, F., Ebner, K., and Lion, T., "Detection and monitoring of virus infections by realtime PCR", *Mol. Aspects of Medicine* 27, 254-298 (2006).

[55] Towner, J. S., et al., "Rapid diagnosis of Ebola hemorrhagic fever by reverse transcription PCR in an outbreak setting and assessment of patient viral load as a predictor of outcome", *J. of Virology* 78, 4330-4341 (2004).

[56] Kuypers, J., Wright, N., Ferrenberg, J., Huang, M., Cent, A., Corey, L., and Morrow, R., "Comparison of Real-Time PCR Assays with Fluorescent-Antibody Assays for Diagnosis of Respiratory Virus Infections in Children", *Journal of Clinical Microbiology* 44, 2382-2388 (2006).

[57] Duan, C., Wang, W., and Xie, Q., "Fabrication of nanofluidic devices", *Biomicrofluidics* 7, 026501 (2013).

[58] Schmidt, H., and Hawkins, A. R., "Optofluidic waveguides: I. Concepts and implementations", *Microfluidics and Nanofluidics* 4, 3-16 (2008).

[59] Hawkins, A. R., and Schmidt, H., "Optofluidic waveguides: II. Fabrication and structures", *Microfluidics and Nanofluidics* 4, 17-32(2008).

[60] Schmidt, H., Yin, D., Barber, J. P., and Hawkins, A. R., "Hollow-core waveguides and 2D waveguide arrays for integrated optics of gases and liquids", IEEE Journal of Selected Topics in Quantum Electronics 11, 519 (2005).

[61] Yin, D., Lunt, E. J., Barman, A., Hawkins, A. R., and Schmidt, H., "Microphotonic control of single molecule fluorescence correlation spectroscopy using planar optofluidics", *Optics Express* 15, 7290-7295 (2007).

[62] Yin, D., Barber, J. P., Deamer, D. W., Hawkins, A. R., and Schmidt, H., "Single-molecule detection sensitivity using planar integrated optics on a chip", *Opt. Lett.* 31, 2136 (2006).

[63] Parks, J. W., Cai, H., Zempoaltecatd, L., Yuzvinsky, T. D., Leake, K., Hawkins, A. R., and Schmidt, H., "Hybrid optofluidic integration", *Lab Chip* 13, 4118-4123 (2013).

[64] Parks, J. W., Olson, M. A., Kim, J., Ozcelik, D., Cai, H., Carrion Jr., R., Patterson, J. L., Mathies, R. A., Hawkins, A. R., and Schmidt, H., "Integration of programmable microfluidics and on-chip fluorescence detection for biosensing applications", *Biomicrofluidics* 8, 054111 (2014).

[65] Cai, H., Parks, J. W., Wall, T. A., Stott, M. A., Stambaugh, A., Alfson, K., Griffiths, A., Mathies, R. A., Carrion, R., Patterson, J. L., Hawkins, A. R., and Schmidt, H., "Optofluidic analysis system for amplification-free, direct detection of Ebola infection", *Scientific Reports* 5, 14494 (2015).

[66] Ozcelik, D., Parks, J. W., Wall, T. A., Stott, M. A., Cai, H., Parks, J. W., Hawkins, A. R., and Schmidt, H., "Optofluidic wavelength division multiplexing for single-virus detection", *PNAS* 112, 12933 (2015).

[67] Liu, S., Zhao, Y., Parks, J. W., Deamer, D. W., Hawkins, A. R., and Schmidt, H., "Correlated Electrical and Optical Analysis of Single Nanoparticles and Biomolecules on a Nanopore-Gated Optofluidic Chip", *Nano Letters* 14, 4816-4820 (2014).

[68] Liu, S., Wall, T. A., Ozcelik, D., Parks, J. W., Hawkins, A. R., and Schmidt, H., "Electro-optical detection of single λ-DNA", *Chem. Comm.* 51, 2084 (2015).

[69] Liu, S., Hawkins, A. R., and Schmidt, H., "Optofluidic devices with integrated solid-state nanopores", *Microchimica Acta* 183, 1275 (2016).

[70] Ozcelik, D., Jain, A., Stambaugh, A., Stott, M. A., Parks, J. W., Hawkins, A. R., and Schmidt, H., "Scalable Spatial-Spectral Multiplexing of Single-Virus Detection Using Multimode Interference Waveguides", *Scientific Reports* 7, 12199 (2017).

[71] Barber, J. P., Conkey, D. B., Lee, J. R., Hubbard, N. B., Howell, L. L., Yin, D., Schmidt, H., and Hawkins, A. R., "Fabrication of Hollow Waveguides with Sacrificial Aluminum Cores", *IEEE Photonics Technology Letters* 17, 363 (2005).

[72] Barber, J. P., Lunt, E., George, Z., Yin, D., Schmidt, H., and Hawkins, A. R., "Integrated Hollow Waveguides with Arch-shaped Cores", *IEEE Photonics Technology Letters* 18, 28 (2006).

[73] Hubbard, N. B., Howell, L. L., Barber, J. P., Conkey, D. B., Hawkins, A. R., and Schmidt, H., "Mechanical models and design rules for on-chip micro-channels with sacrificial cores", *Journal of Micromechanics and Microengineering* 15, 720, (2005).

[74] Lunt, E. J., Measor, P., Phillips, B. S., Kuhn, S., Schmidt, H., and Hawkins, A. R., "Improving solid to hollow core transmission for integrated ARROW waveguides", *Optics Express* 16, 20981-20986 (2008).

[75] Lunt, E. J., Wu, B., Keeley, J. M., Measor, P., Schmidt, H., and Hawkins, A. R., "Improving Hollow ARROW Waveguides on Self-Aligned Pedestals for Improved Geometry and Transmission", *IEEE Phot. Tech. Let.* 22, 1041 (2010).

[76] Zhao, Y., Jenkins, M., Measor, P., Leake, K., Liu, S., Schmidt, H., and Hawkins, A. R., "Hollow Waveguides with Low Intrinsic Photoluminescence Fabricated with $Ta_2O_5$ and $SiO_2$ Films," *Applied Physics Letters* 98, 091104 (2011).

[77] Zhao, K., Leake, K., Measor, P., Jenkins, M., Keeley, J., Schmidt, H., and Hawkins, A. R., "Optimization of Interface Transmission between Integrated Solid Core and Optofluidic Waveguides", *IEEE Photonics Technology Letters* 24, 46-48 (2012).

[78] Du, K., Cai, H., Park, M., Wall, T., Stott, M., Alfson, K., Griffiths, A., Carrion, R., Patterson, J. L., Hawkins, A. R., Schmidt, H., and Mathies, R. A., "Multiplexed Efficient On-Chip Sample Preparation and Sensitive Amplification-Free Detection of Ebola Virus", *Biosensors Bioelectronics* 91, 489-496 (2017).

[79] Du, K., Park, M., Griffiths, A., Carrion, R., Patterson, J., Schmidt, H., and Mathies, R., "Microfluidic System for Detection of Viral RNA in Blood Using a Barcode Fluorescence Reporter and a Photocleavable Capture Probe", *Anal. Chem.* 89, 12433-12440 (2017).

[80] Cai, H., Stott, M. A., Ozcelik, D., Parks, J. W., Hawkins, A. R., and Schmidt, H., "On-chip wavelength multiplexed detection of cancer DNA biomarkers in blood", *Biomicrofluidics* 10, 064116 (2016).

[81] Holmes, M. R., Rudenko, M., Measor, P., Shang, T., Hawkins, A. R., and Schmidt, H., "Micropore and nanopore fabrication in hollow antiresonant reflecting optical waveguides", *J. Micro/Nanolith. MEMS MOEMS* 9, 023004 (2010).

[82] Rudenko, M. I., Holmes, M. R., Ermolenko, D. N., Lunt, E. J., Gerhardt, S., Noller, H. F., Deamer, D. W., Hawkins, A. R., and Schmidt, H., "Controlled gating and electrical detection of single 50S ribosomal subunits through a solid-state nanopore in a microfluidic chip", *Biosensors and Bioelectronics* 29, 34-39 (2011).

[83] Liu, S., Yuzvinsky, T. D., and Schmidt, H., "Effect of Fabrication-Dependent Shape and Composition of Solid-State Nanopores on Single Nanoparticle Detection", *ACS Nano* 7, 5621-5627 (2013).

[84] Brasil, P. et al., "Zika Virus Infection in Pregnant Women in Rio de Janeiro", *N Engl J Med* 375, 2321-2334 (2016).

[85] Corman, V. M. et al., "Assay optimization for molecular detection of Zika virus", *Bull World Health Organ* 94, 880-892 (2016).

[86] Barzon, L. et al., "Infection dynamics in a traveller with persistent shedding of Zika virus RNA in semen for six months after returning from Haiti to Italy", *Euro Surveill* 21, 30316 (2016).

[87] J. W. Parks; A. Stambaugh; M. A. Stott; G. M. Meena; A. R. Hawkins; H. Schmidt, "Dual detection of Zika virus nucleic acid and protein using a multi-mode interference waveguide platform", Proceedings of the IEEE Photonics Conference (IPC), DOI: 10.1109/IPCon.2017.8116197 (2017).

[88] Measor, P., Kuhn, S., Lunt, E. J., Phillips, B. S., Hawkins, A. R., and Schmidt, H., "Hollow-core Waveguide Characterization by Optically Induced Particle Transport", *Optics Letters* 33, 672-674 (2008).

[89] Measor, P., Kuhn, S., Lunt, E. J., Philips, B. S., Hawkins, A. R., and Schmidt, H., "Multi-mode mitigation in an optofluidic chip for particle manipulation and sensing", *Optics Express* 17, 24342 (2009),

[90] Kühn, S., Measor, P., Lunt, E. J., Phillips, B. S., Deamer, D. W., Hawkins, A. R., and Schmidt, H., "Loss-based optical trap for on-chip particle analysis", *Lab Chip* 9, 2212 (2009).

[91] Kühn, S., Measor, P., Lunt, E. J., Phillips, B. S., Hawkins, A. R., and Schmidt, H., "Optofluidic particle concentration by a long-range dual-beam trap", *Optics Letters* 34, 2306-2308 (2009).

[92] Kühn, S., Lunt, E. J., Philips, B. S., Hawkins, A. R., and Schmidt, H., "Ultralow power trapping and fluorescence detection of single particles on an optofluidic chip", *Lab Chip* 10, 189 (2010).

[93] Song, H., Qi, J., Haywood, J., Shi, Y., and Gao, G. F., "Zika virus NS1 structure reveals diversity of electrostatic surfaces among flaviviruses", *Nat. Struct. Mol. Biol.* 23, 456-458 (2016).

[94] Kumar, S., Xuan, J., Lee, M. L., Tolley, D., Hawkins, A. R., and Woolley, A. T., "Thin-Film Microfabricated Nanofluidic Arrays for Size-Selective Protein Fractionation," *Lab on a Chip* 13, 4591-4598 (2013).

[95] Nam, J., Thaxton, C. S., and Mirkin, C. A., "Nanoparticle-Based Bio-Bar Codes for the Ultrasensitive Detection of Proteins", *Science* 301, 1884-1886 (2003).

[96] Boonjob, W., "An Overview about Recent Advances of Micro-Solid Phase Extraction in Flow Based Techniques", *Austin J Anal Pharm Chem.* 1, 1006 (2014).

[97] Hwang, K., Kwon, S. H., Jung, S., Namkoong, K., Jung, W., Kim, J., Suh, K., and Huh, N., "Solid Phase DNA Extraction with a Flexible Bead-Packed Microfluidic Device to Detect Methicillin-Resistant *Staphylococcus aureus* in Nasal Swabs", *Anal. Chem.* 84 7912-7918 (2012).

[98] Bylda, C., Thiele, R., Kobold, U., and Volmer, D. A., "Recent advances in sample preparation techniques to overcome difficulties encountered during quantitative analysis of small molecules from biofluids using LC-MS/MS", *Analyst* 139, 2265-2276 (2014).

[99] Safarik, I. and Safarikova, M., "Magnetic techniques for the isolation and purification of proteins and peptides", *Biomagnetic Research and Technology* 2, doi: 10.1186/1477-044x-2-7 (2004).

[100] Odabasi, M. and Denizil, A., "Polyhydroxyethylmethacrylate-based magnetic DNA-affinity beads for anti-DNA antibody removal from systemic lupus erythematosus patient plasma", *J Chromatogr B,* 760, 137-148 (2001).

[101] Quitadamo, I. J., Kostman, T. A., Schelling, M. E., and Franceschi V. R., "Magnetic bead purification as a rapid and efficient method for enhanced antibody specificity for plant sample immunoblotting and immunolocalization", *Plant Sci.* 153, 7-14 (2000).

[102] Ozkara, S., Akgol, S., Canak, Y., and Denizli, A., "A novel magnetic adsorbent for immunoglobulin-G purification in a magnetically stabilized fluidized bed", *Biotechnol Progress* 20, 1169-1175 (2004).

[103] Zika Experimental Science Team, "ZIKV-001: Infection of three rhesus macaques with French Polynesian Zika virus", https://zika.labkey.com/project/oconnor/ZTKV-001/begin.view (2016).

[104] http://www.biofronttech.com/product/research-reagents-zika-virus-reagents-zika-virus-ns1-elisa/zika-virus-ns1-elisa/1607015/

[105] Schudel, B. R., Choi, C. J., Cunningham, B. T., and Kenis, P. J. A., "Microfluidic chip for combinatorial mixing and screening of assays", *Lab Chip* 9, 1676-1680 (2009).

[106] Kim, J., Kang, M., Jensen, E. C., and Mathies, R. A., "Lifting gate polydimethylsiloxane microvalves and pumps for microfluidic control", *Anal. Chem.* 84, 2067-2071 (2012).

[107] Kim, J., Stockton, A. M., Jensen, E. C., and Mathies, R. A., "Pneumatically actuated microvalve circuits for programmable automation of chemical and biochemical analysis", *Lab Chip* 16, 812-819 (2016).

[108] Larsen, E. K. U., Mikkelsen, M. B. L., and Larsen, N. B., "Protein and cell patterning in closed polymer channels by photoimmobilizing proteins on photografled poly(ethylene glycol) diacrylate", *Biomicrofluidics* 8, 064127 (2014).

[109] Ruiz-Taylor, L. A., Martin, T. L., and Wagner, P., "X-ray Photoelectron Spectroscopy and Radiometry Studies of Biotin-Derivatized Poly(L-lysine)-grafted-Poly(ethylene glycol) Monolayers on Metal Oxides", *Langmuir* 17, 7313-7322 (2001).

[110] Ruiz-Taylor, L. A., Martin, T. L., Zaugg, F. G., Witte, K., Indermuhle, P., Nock, S., and Wagner, P., "Monolayers of derivatized poly(L-lysine)-grafted poly(ethylene glycol) on metal oxides as a class of biomolecular interfaces", *PNAS* 98, 852-857 (2000).

[111] Yang, L., Okamura, Y., and Kimura, H., "Surface modification on polydimethylsiloxane-based microchannels with fragmented poly(l-lactic acid) nanosheets", *Biomicrofluidics* 9, 064108 (2015).

[112] Shin, Y. S., Cho, K., Lim, S. H., Chung, S., Park, S., Chung, C., Han, D., and Chang, J. K., "PDMS-based micro PCR chip with Parylene coating", *J. Micromech. Microeng.* 13, 768-774 (2003).

What is claimed is:

1. A method of detecting a plurality of target molecules, comprising:
    providing a plurality of microbeads, where each microbead of the plurality of microbeads comprises a surface comprising a plurality of capture molecules that each specifically binds one or more of the plurality of target molecules;
    contacting a sample suspected of containing the plurality of target molecules with the plurality of microbeads under conditions that allow binding of the plurality of capture molecules to the plurality of target molecules;
    applying the plurality of microbeads to a first microfluidic chip, the microfluidic chip comprising a membrane, the membrane comprising a first side, a second side, and a pore, the pore comprising a first opening on the first side of the membrane and a second opening on the second side of the membrane, the pore further comprising an ionic current flowing from the first side to the second side and a capture volume;
    trapping the plurality of microbeads within the capture volume of the pore using optical trapping or fluid flow;
    while the plurality of microbeads are trapped within the capture volume of the pore, releasing the plurality of target molecules from the plurality of capture molecules, such that the plurality of target molecules pass through the pore; and
    measuring the change in ionic current, thereby detecting the plurality of target molecules as they pass through the pore.

2. The method of claim 1, wherein the plurality of capture molecules comprises an antibody or an antigen binding fragment thereof.

3. The method of claim 1, wherein the plurality of target molecules comprises a polypeptide or nucleic acid.

4. The method of claim 3, wherein the plurality of target molecules comprises a nucleic acid and wherein the plurality of capture molecules comprises a complimentary nucleic acid.

5. The method of claim 1, wherein the sample is selected from blood or any fraction thereof, urine, sweat, sputum, saliva, feces, or semen.

6. The method of claim 1, wherein the contacting of the sample with the plurality of microbeads is performed in a second microfluidic chip.

7. The method of claim 6, wherein the microfluidic chip comprises an automaton network.

8. The method of claim 1, wherein the plurality of microbeads are trapped on the first side of the membrane and where the opening of the pore on the first side of the membrane is greater than 1 µm in diameter and where the opening of the pore on the second side of the membrane is less than 1 µm in diameter.

9. The method of claim 1, wherein the plurality of microbeads are trapped on the first side of the membrane and where the opening of the pore on the first side of the membrane is less than 1 µm in diameter and where the opening of the pore on the second side of the membrane is less than 1 µm in diameter.

10. The method of claim 8, wherein the opening of the pore on the second side of the membrane is less than 100 nm.

11. The method of claim 8, wherein the opening of the pore on the second side of the membrane is less than 50 nm.

12. The method of claim 1, wherein releasing the plurality of target molecules comprises applying heat to the microbead or raising or lowering the pH in the solution near the microbead.

13. A system, comprising:
 a plurality of microbeads, each microbead of the plurality of microbeads comprising a surface comprising a plurality of capture molecules, where each of the capture molecules specifically binds to one or more of a plurality of target molecules;
 a first microfluidic chip comprising a membrane, the membrane comprising a first side, a second side, and a pore, the pore comprising a first opening on the first side of the membrane and a second opening on the second side of the membrane, the pore further comprising a capture volume, the microfluidic chip further comprising an element configured to release a target molecule from the capture molecule;
 wherein the first microfluidic chip is configured to trap the plurality of microbeads within the capture volume of the pore using optical trapping or fluid flow and configured to signal when the plurality of target molecules pass through the pore.

14. The system of claim 13, wherein the opening of the pore on the first side of the membrane is greater than 1 µm in diameter and where the opening of the pore on the second side of the membrane is less than 1 µm in diameter.

15. The system of claim 13, wherein the plurality of microbeads are trapped on the first side of the membrane and where the opening of the pore on the first side of the membrane is less than 1 µm in diameter and where the opening of the pore on the second side of the membrane is less than 1 µm in diameter.

16. The system of claim 14, wherein the opening of the pore on the second side of the membrane is less than 100 nm.

17. The system of claim 14, wherein the opening of the pore on the second side of the membrane is less than 50 nm.

18. The system of claim 13, wherein the element is configured to heat or raise or lower the pH of the solution.

* * * * *